United States Patent [19]

Burdeska et al.

[11] Patent Number: 4,674,229
[45] Date of Patent: Jun. 23, 1987

[54] PHENYLPYRIMIDINES AS ANTIDOTES FOR PROTECTING CULTIVATED PLANTS AGAINST PHYTOTOXIC DAMAGE CAUSED BY HERBICIDES

[75] Inventors: Kurt Burdeska, Basel; Guglielmo Kabas, deceased, late of Aesch, by Anni Kabas-Maskulinski, legal heir; Hans-Georg Brunner, Lausen; Werner Föry, Basel, all of Switzerland

[73] Assignee: Ciba-Geigy Corporation, Ardsley, N.Y.

[21] Appl. No.: 667,705

[22] Filed: Nov. 2, 1984

Related U.S. Application Data

[60] Division of Ser. No. 486,651, Apr. 20, 1983, Pat. No. 4,493,726, which is a continuation-in-part of Ser. No. 331,853, Dec. 17, 1981, abandoned.

[30] Foreign Application Priority Data

Apr. 8, 1981 [CH] Switzerland .................... 9522/80
Apr. 8, 1981 [CH] Switzerland .................... 2363/81

[51] Int. Cl.$^4$ ............................................. A01N 25/32
[52] U.S. Cl. ........................................ 47/57.6; 71/92
[58] Field of Search ............................. 71/92; 47/57.6

[56] References Cited

U.S. PATENT DOCUMENTS 3,503,976  3/1970  Reicheneder et al. .............. 544/326

Primary Examiner—Catherine L. Mill
Attorney, Agent, or Firm—Edward McC. Roberts; Meredith C. Findlay

[57] ABSTRACT

Phenylpyrimidines of the formula I as defined below are suitable as antidotes for protecting cultivated plants from phytotoxic effects caused by herbicides. These antidotes, either together with the herbicides or also by themselves, are applied to the plants or incorporated in the soil in which the plants grow, or they are used to treat the seeds of the plants. Suitable herbicides are those belonging to the class of the haloacetanilides, haloacetamides, thiocarbamates, carbamates, nitroanilides, triazines, phenylureas, haloacetic acids, phenoxy- and pyridyloxyphenoxyalkanecarboxylic acid derivatives, benzoic acid derivatives etc. The phenylpyrimidines have the formula I

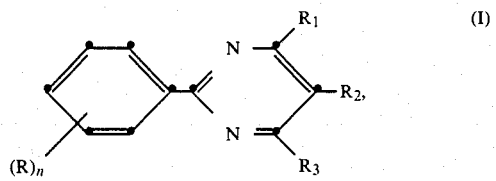

wherein for example, $R_1$ and $R_3$ are halogen.

16 Claims, No Drawings

PHENYLPYRIMIDINES AS ANTIDOTES FOR PROTECTING CULTIVATED PLANTS AGAINST PHYTOTOXIC DAMAGE CAUSED BY HERBICIDES

CROSS-REFERENCE TO RELATED APPLICATION

This is a division of application U.S. Ser. No. 486,651 filed on Apr. 20, 1983, now U.S. Pat. No. 4,493,726, which is a continuation-in-part of application Ser. No. 331,853 filed on Dec. 17, 1981, now abandoned.

The present invention relates to a method of and a composition for protecting cultivated plants from the phytotoxic effects of herbicides. In the method of this invention, the phenylpyrimidines of the formula I below are applied to the crops of cultivated plants simultaneously or shortly afterwards with the herbicide, or a composition which, in addition to containing the herbicide, also contains a phenylpyrimidine of the formula I, is applied to the crops. The invention also relates to the compositions which contain phenylpyrimidines of the formula I.

The phenylpyrimidines of this invention have the formula I

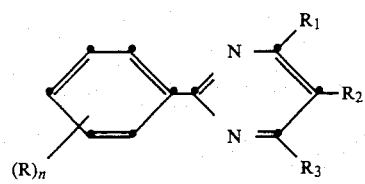

in which
n is an integer from 1 to 5,
R is hydrogen, halogen, cyano, nitro or hydroxyl, a $C_1$–$C_6$alkyl, $C_1$–$C_6$alkoxy or $C_1$–$C_6$alkylthio group, which is unsubstituted or mono- or polysubstituted by halogen, $C_1$–$C_6$alkoxy, $C_2$–$C_{12}$alkoxyalkyl, $C_1$–$C_6$alkylcarbonyl, $C_1$–$C_6$alkylcarbonyloxy, $C_1$–$C_6$alkoxycarbonyl, $C_2$–$C_6$alkenylcarbonyl or $C_2$–$C_6$alkynylcarbonyl, di($C_1$–$C_6$)alkylamino, $C_1$–$C_6$-alkylenedioxy, phosphonyl or $C_1$–$C_6$alkylphosphonyl; or R is a $C_2$–$C_6$alkenyl or $C_2$–$C_6$alkenyloxy group or the formyl or carboxyl group; or it is a carbonyl or carbonyloxy group which is substituted by $C_1$–$C_6$alkyl, $C_1$–$C_6$haloalkyl, $C_1$–$C_6$alkoxy, $C_2$–$C_6$alkenyl, $C_2$–$C_6$alkynyl, amino, di($C_1$–$C_6$)alkylamino, or by a 5- to 6-membered saturated heterocyclic ring which is bound through the nitrogen atom; or it is an amino group which is unsubstituted or substituted by $C_1$–$C_6$alkyl, $C_1$–$C_6$alkoxy, $C_1$–$C_6$alkylcarbonyl; or is an ureido radical which is unsubstituted or substituted by $C_1$–$C_6$alkyl or $C_1$–$C_6$alkoxy or it is the sulfonyl, a $C_1$–$C_6$alkylsulfonyl, sulfamoyl, $C_1$–$C_6$alkylsulfamoyl or $C_1$–$C_6$alkylcarbonylsulfamoyl-rest, $R_1$ and $R_3$, each independently of the other, are halogen, cyano, hydroxyl, sulfhydryl, a $C_1$–$C_6$alkyl, $C_1$–$C_6$alkoxy or $C_1$–$C_6$alkylthio radical, which is unsubstituted or substituted by halogen or $C_1$–$C_6$alkoxy; a $C_2$–$C_6$alkenyl or $C_2$–$C_6$alkynyl radical, or a $C_3$–$C_6$cycloalkyl radical, an amino, $C_1$–$C_6$alkylamino or di($C_1$–$C_6$)alkylamino group, a 5- to 6-membered saturated heterocyclic ring which is bound through the nitrogen atom; a phenyl or phenoxy-rest and $R_2$ is hydrogen, halogen, $C_1$–$C_6$alkyl, $C_1$–$C_6$haloalkyl or phenyl.

Alkyl by itself or as moiety of another substituent comprises branched or unbranched alkyl groups which contain the indicated number of carbon atoms. Examples of such alkyl groups are: methyl, ethyl, propyl, isopropyl, butyl, isobutyl, sec-butyl, tert-butyl, as well as the higher homologs amyl, isoamyl, hexyl, heptyl, octyl, together with their isomers. The alkenyl and alkynyl groups can likewise be straight chain or branched. Cycloalkyl groups are cyclopropyl, cyclobutyl, cyclopentyl and cyclohexyl.

The phenylpyrimidines of the formula I are most suitable for protecting cultivated plants such as sorghum, rice, maize, cereals (wheat, rye, barley, oats), cotton, sugar beet, sugar cane, soybeans etc., from attack by aggressive agrochemicals, especially by herbicides belonging to a wide variety of compound classes, e.g. triazines, phenylurea derivatives, carbamates, thiocarbamates, haloacetanilides, halophenoxyacetates, substituted phenoxyphenoxyacetates and -propionates, substituted pyridyloxyphenoxyacetates and -propionates, benzoic acid derivatives etc., where these compounds do not have a selective action or do not act selectively enough, i.e. where they also damage the cultivated plants to a greater or lesser extent in addition to the weeds to be controlled. The invention also relates to compositions which contain these phenylpyrimidines of the formula I, together with herbicides.

Particularly suitable antidotes are the phenylpyrimidines of the formula I, wherein n is an integer of from 1 to 5, R is hydrogen, halogen, cyano, nitro, hydroxyl, $C_1$–$C_6$alkyl, $C_1$–$C_6$alkoxy, $C_1$–$C_6$haloalkyl, $C_2$–$C_6$alkenyl, $C_2$–$C_6$haloalkenyl, $C_2$–$C_6$alkynyl, amino, $C_1$–$C_6$alkylamino, $C_1$–$C_6$alkylcarbonylamino, carboxy, $C_1$–$C_6$alkylcarbonyl, $C_1$–$C_6$alkoxycarbonyl, sulfonyl, $C_1$–$C_6$alkylsulfonyl, sulfamoyl, $C_1$–$C_6$alkylsulfamoyl, $C_1$–$C_6$-alkylcarbonylsulfamoyl, $R_1$ and $R_3$ independently of each other are halogen and $R_2$ is hydrogen or chlorine.

Important compounds are phenylpyrimidines of the formula I, wherein n is 1 and R is in the para-position to the pyrimidine-rest and represents hydrogen, halogen, $C_1$–$C_6$alkyl, hydroxyl, $C_1$–$C_6$alkoxy; $R_1$ and $R_3$ are halogen and $R_2$ is hydrogen, especially
2-phenyl-4,6-dichloropyrimidine,
2-phenyl-4,6-dibromopyrimidine,
2-para-tolyl-4,6-dichloropyrimidine,
2-(4-chlorophenyl)-4,6-dichloropyrimidine,
2-(4-methoxyphenyl)-4,6-dichloropyrimidine,
2-(4-hydroxyphenyl)-4,6-dichloropyrimidine,
2-(3-nitrophenyl)-4,6-dichloropyrimidine and
2-(3-chloro-4-fluorophenyl)-4,6-dichloropyrimidine.

Various compounds which are able to antagonise specifically the harmful effects of a herbicide on cultivated plants have already been proposed as safeners or antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows, or as tank mixture together with the herbicide, before or after emergence of the plants.

For example, British patent specification No. 1 277 557 discloses the treatment of seed and seedlings of wheat and sorghum with certain esters and amides of oxamic acid from attack by N-methoxymethyl-2',6'-diethyl-chloroacetanilide (Alachlor). Other publications (German Offenlegungsschrift specifications Nos. 1 952 910 and 2 245 471, and French patent specification No. 2 021 611), propose antidotes for the treatment of cereals, maize seeds and rice seeds to protect them from attack by herbicidal thiocarbamates. In German patent specification No. 1 576 676 and U.S. Pat. No. 3,131,509, hydroxyaminoacetanilides and hydantoins are suggested for protecting cereal seeds against carbamates such as IPC, CIPC, etc. Further development, however, has shown all these preparations to be unsatisfactory.

Surprisingly, phenylpyrimidines of the formula I have the property of protecting cultivated plants from attack by aggressive agrochemicals, in particular from herbicides belonging to a wide range of compound classes, for example chloroacetanilides, chloroacetamides, carbamates and thiocarbamates, diphenyl ethers and nitrodiphenyl ethers, benzoic acid derivatives, triazines and triazinones, phenylureas, nitroanilines, oxdiazolones, pyridyloxyphenoxy derivatives, phosphates and pyrazoles, where these compounds are not tolerated or are insufficiently tolerated by the cultivated plants.

The phenylpyrimidines of this invention preferably protect herbicides belonging to the classes of the chloroacetanilides, chloroacetamides, thiocarbamates, and phosphates.

Depending on the particular purpose, a safener or antidote of the formula I can be used for pretreating the seeds of the cultivated plant or incorporated in the soil before or after sowing, or else applied by itself alone or together with the herbicide before or after emergence of the plants. In principle, therefore, the treatment of the plant or seeds can be carried out independently of the time of application of the phytotoxic chemical. However, the treatment can also be carried out simultaneously (tank mixture). Preemergence treatment includes both the treatment of the crop area before sowing (ppi=preplant incorporation), and the treatment of the sown crop areas in which the plants have not yet emerged.

The rates of application in which the antidote is employed in relation to the herbicide depend largely on the mode of application. Where a field treatment is carried out, either as tank mixture or if herbicide and antidote are applied separately, the ratio of antidote to herbicide is usually from 1:100 to 10:1, with the preferred range however being from 1:5 to 8:1, most preferably 1:1.

When dressing seeds and taking similar protective measures, however, much smaller amounts of antidote are required in comparison e.g. with the amounts of herbicide employed later per hectare of crop area. For seed dressing, 0.1 to 10 g of antidote is usually required per kg of seeds, with the preferred amount being from 1 to 2 g. If the antidote is to be applied shortly before sowing by seed soaking, then e.g. antidote solutions which contain the active ingredient in a concentration of 1–10 000 ppm, preferably 100–1000 ppm, are used.

Protective measures such as seed dressing with an antidote of the formula I and a possible later field treatment with agrochemicals, normally follow at a greater interval of time. Pretreated seeds and plants can come into contact later with different chemicals in agriculture, horticulture and forestry.

Accordingly, the invention also relates to plant protection compositions which contain, as active ingredient, an antidote of the formula I together with conventional carriers. If appropriate or desired, such compositions can additionally be mixed with the chemical against the action of which it is desired to protect the cultivated plant, for example with a herbicide.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals such as wheat, rye, barley and oats, and also in particular rice, sorghum, cotton, sugar beet, sugar cane, soybeans, beans and peas.

The antidote will be employed whereever it is intended to protect a cultivated plant from the phytotoxicity of a chemical.

The following compounds are cited as examples of herbicides against whose effects it is desired to protect cultivated plants:

Chloroacetanilides: 2-chloro-2',6'-diethyl-N-(2''-propoxyethyl)acetanilide ("Propachlor"), 2-chloro-6'-ethyl-N-(2''-methoxy-1''-methylethyl)-acet-o-toluidide ("Metolachlor"), 2-chloro-2',6'-diethyl-N-(butoxymethyl)acetanilide ("Butachlor"), 2-chloro-6'-ethyl-N-(ethoxymethyl)acet-o-toluidide ("Acetochlor"), 2-chloro-6'-ethyl-N-(2''-propoxy-1''-methylethyl)acet-o-toluidide, 2-chloro-2',6'-dimethyl-N-(2''-methoxy-1''-methylethyl)acetanilide, 2-chloro-2',6'-dimethyl-N-(2''-methoxyethyl)acetanilide ("Dimethachlor"), 2-chloro-2',6'-diethyl-n-(pyrazol-1-ylmethyl)acetanilide, 2-chloro-6'-ethyl-N-(pyrazol-1-ylmethyl)acet-o-toluidide, 2-chloro-6'-ethyl-N-(3,5-dimethylpyrazol-1-ylmethyl)acet-o-toluidide, 2-chloro-6'-ethyl-N-(2''-butoxy-1''-methylethyl)acet-o-toluidide ("Metazolachlor"), 2-chloro-6'-ethyl-N-(2''-butoxy-1''-(methylethyl)acet-o-toluidide, 2-chloro-2'-trimethylsilyl-N-(butoxymethyl)acetanilide, 2-chloro-2',6'-diethyl-N-(methoxymethyl)acetanilide ("Alachlor") and 2-chloro-2',6'-diethyl-N-(ethoxycarbonylmethyl)acetanilide.

Chloroacetamides: N-[1-isopropyl-2-methylpropen-1-yl-(1)]-N-(2'-methoxyethyl)-chloroacetamide.

Carbamates and thiocarbamates: N(3',4'-dichlorophenyl)propionanilide ("Propanil"), S-4-chlorobenzyldiethyl-thiocarbamate ("Thiobencarb"), S-ethyl-N,N-hexamethylene-thiocarbamate ("Molinate"), S-ethyl-dipropyl-thiocarbamate ("EPTC"), N,N-di-sec-butyl-S-benzyl-thiocarbamate (Drepamon), S-(2,3-dichloroallyl)-diisopropylthiocarbamate and S(2,3,3-trichloroallyl)-diisopropylthiocarbamate ("Di- and Tri-allate"), 1-(propylthiocarbonyl)-decahydroquinaldine, S-4-benzyldiethylthiocarbamate and also corresponding sulfinylcarbamates.

Diphenylethers and nitrodiphenyl ethers: 2,4-dichlorophenyl-4'-nitrophenyl ether ("Nitrofen"), 2-chloro-1-(3'-ethoxy-4'-nitrophenoxy)-4-trifluoromethylbenzene ("Oxyfluorfen"), 2',4'-dichlorophenyl-3-methoxy-4-nitrophenyl ether ("Chlormethoxynyl"), methyl 2-[4'-(2'',4''-dichlorophenoxy)phenoxy)propionate, N-(2'-methoxyethyl)-2-[5'-(2''-chloro-4''-trifluoromethylphenoxy)phenoxy]propionamide.

Benzoic acid derivatives: methyl 5-(2',4'-dichlorophenoxy)-2-nitrobenzoate ("Bifenox"), 5-(2'-chloro-4'- trifluoromethylphenoxy)-2-nitrobenzoic acid ("Acifluorfen"), 2,6-dichlorobenzonitrile ("Dichlobenil").

Triazines and triazinones: 2,4-bis(isopropylamino)-6-methylthio-1,3,5-triazine ("Prometryn"), 2,4-bis(ethylamino)-6-methylthio-1,3,5-triazine ("Simetryn"), 2-(1',2'-dimethylpropylamino)-4-ethylamino-6-methylthio-1,3,5-triazine ("Dimethametryn"), 4-amino-6-tert-butyl-4,5-dihydro-3-methylthio-1,2,4-triazin-5-one ("Metribuzin").

Phenylureas: N-(3'-isopropylphenyl)-N',N'-dimethyl urea ("Isoproturon"), N-(3',4'dimethylbenzyl)-N'-4-tolyl urea ("Dimuron"), N-(3'-chloro-4' -isopropylphenyl)-N',N'-(3-methyl-pentamethylen-1,5-yl) urea.

Nitroanilines: 2,6-dinitro-N,N-dipropyl-4-trifluoromethylaniline ("Trifluralin"), N-(1'-ethylpropyl)-2,5-dinitro-3,4-xylidene ("Pendimethalin").

Oxadiazolones: 5-tert-butyl-3-(2',4'-dichloro-5'-isopropoxyphenyl)-1,3,4-oxadiazol-2-one ("Oxdiazon").

Pyridyloxyphenoxy derivatives: 2-propinyl-2-[4'-(3",5"-dichloropyridyl-2"-oxy)phenoxy]-propionate.

Phosphates: S-2-methylpiperidino-carbonylmethyl-O,O-dipropylphosphoro-dithioate ("Piperophos").

Pyrazoles: 1,3-dimethyl-4-(2',4'-dichlorobenzoyl)-5-(4'-tolylsulfonyloxy)pyrazole.

The phenylpyrimidines of the formula I which act as antidotes may optionally be employed after application of the agrochemical or also simultaneously with it.

Many phenylpyrimidines of this invention are novel, whilst others are known compounds. Phenylpyrimidines are used as intermediates in the manufacture of dyes, in which connection attention is drawn to e.g. British patent specification No. 1 502 912 or to published European patent applications Nos. 20 298 and 31 796. They are also known as intermediates of pharmacologically active compounds, q.v. J. Med. Chem. 1978 (21), pp. 123–126, or they are met with elsewhere in the chemical literature, q.v. Bull. Soc. Chem. Jap. 44 (8), pp. 2182–5.

The phenylpyrimidines of the formula I can be obtained by known synthesis routes. The 2-phenylpyrimidine ring is formed e.g. by condensation of a phenylamidine with a malonic acid derivative.

The 2-phenylpyrimidines are obtained by condensing a phenylamidine with a dialkyl malonate in alcoholic solution in the presence of a base

| Antidote compound | Rate of application in kg/ha | Herbicide rate of application in kg/ha | Protective action in % |
|---|---|---|---|
| 50 | 0.5 | 0.5 | 25 |
| 53 | 0.25 | 0.25 | 25 |
| 54 | 0.5 | 0.5 | 25 |
| Herbicide: 2-chloro-6'-ethyl-N—(2"methoxy-1"methylethyl)-acet-o-toluidide, "Metolachlor" | | | |
| 1 | 3 | 0.75 | 37.5 |
| Herbicide: 2-chloro-6'-ethyl-N—(ethoxymethyl)-acet-o-toluidide "Acetochlor" | | | |
| 1 | 0.25 | 0.25 | 25 |
| 2 | 0.25 | 0.25 | 12.5 |
| 49 | 0.25 | 0.25 | 12.5 |
| 50 | 0.25 | 0.25 | 12.5 |
| 53 | 0.25 | 0.25 | 12.5 |
| 54 | 0.25 | 0.25 | 12.5 |
| Herbicide: 2,6-dinitro-N,N—dipropyl-4-trifluoromethylaniline "Trifluralin" | | | |
| 1 | 1 | 1 | 37.5 |
| 2 | 1 | 1 | 25 |
| 50 | 1 | 1 | 12.5 |
| 53 | 1 | 1 | 37.5 |
| 54 | 1 | 1 | 25 |

-continued

| Antidote compound | Rate of application in kg/ha | Herbicide rate of application in kg/ha | Protective action in % |
|---|---|---|---|
| Herbicide: 2,6-dichlorobenzonitrile, "Dichlobenil" | | | |
| 1 | 0.5 | 0.5 | 12.5 |
| 2 | 0.5 | 0.5 | 12.5 |
| 49 | 0.5 | 0.5 | 25 |
| 50 | 0.5 | 0.5 | 25 |
| 53 | 0.5 | 0.5 | 25 |
| 54 | 0.5 | 0.5 | 25 |
| Herbicide: S—2,3-dichloroallyl-diisopropylthiocarbamate "Di-allate" | | | |
| 1 | 4 | 4 | 12.5 |
| 2 | 4 | 4 | 25 |
| 49 | 4 | 4 | 12.5 |
| 50 | 4 | 4 | 25 |
| 53 | 4 | 4 | 25 |
| 54 | 4 | 4 | 25 | and then, if desired, replacing the hydroxyl groups of the resultant 2-phenyl-4,6-dihydroxypyrimidine of the formula IV by halogen atoms with a halogenating agent (phosphoroxy chloride, phosphoroxy bromide, sulfuryl chloride, bromosuccinimide etc.) and, if desired, replacing these halogen atoms in turn by further radicals $R_1$ and $R_3$.

If $R_2$ is hydrogen, this can be replaced e.g. by treatment with chlorine or bromine in a polar solvent, e.g. glacial acetic acid.

The halogen atoms in the positions 4, 5, and 6 of the pyrimidine ring can in turn be replaced, in known manner, by alcohols, mercaptans or amines.

The following publications, for example, are cited as references: J. Chem. Soc. 1965, pp. 5467–5473, J. prakt. Chem. 312 (1970), pp. 494–506, J. Chem. Soc. Perkin Trans. 1 1977, pp. 2285–6.

Phenylpyrimidines in which $R_1$ is an alkyl or phenyl group are obtained e.g. by condensation of a phenylamidine with an alkyl ester of an acetoacetic acid:

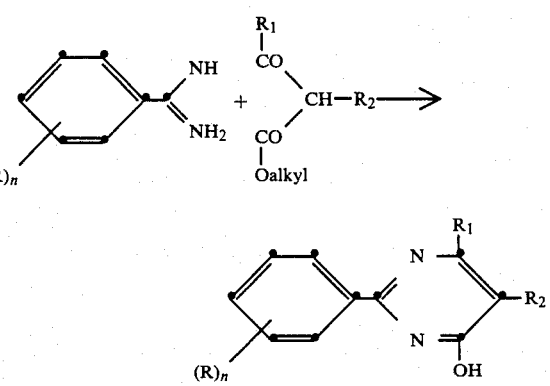

Here too the —OH group can be replaced in known manner by a halogen atom, which in turn can be replaced by an alcohol, a thiol or an amine.

It is also possible to prepare e.g. 2-phenyl-4,6-dichloropyrimidine and 2-phenyl-4-chloro-6-hydroxypyrimidines by reaction of chlorobenzylidene-carbamoyl chlorides with an aliphatic nitrile in the presence of hydrogen chloride:

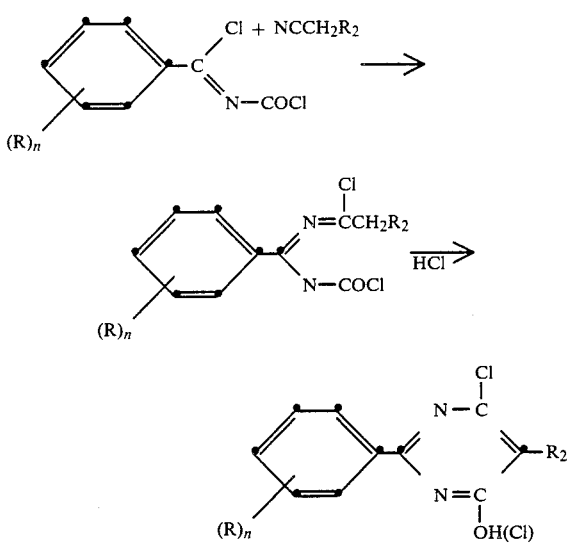

q.v. Bull. Soc. Chem. Japan 44 (1971), pp. 2182-2185.

2-Phenyl-4,6-dichloropyrimidine can be obtained e.g. in accordance with Ang. Chemie 89 (1977), pp. 816-817, e.g. by condensation of a N-phenyl cyanamide and a N,N-dialkyl amide in POCl$_3$ at 100° C.:

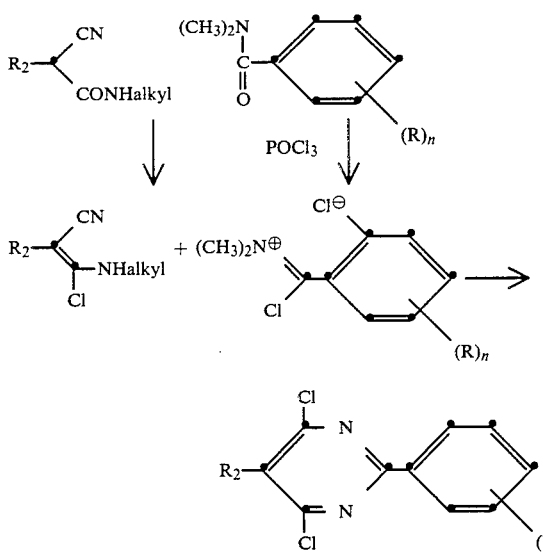

In the above formulae, R, R$_2$ and n are as defined for formula I.

The synthesis of such compounds or the exchange of radicals R$_1$, R$_2$ and R$_3$ by other substituents cited in the definition are procedures which are known per se. As regards the preparation of these compounds attention is drawn to the Examples or to the literature. A further reference is also "The Chemistry of Heterocyclic Compounds", 16, Interscience Publishers, New York 1962, pp. 119 ff.

The compounds of formula I can be used by themselves alone or together with the compounds which it is desired to antagonise.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polmyer substances. Just like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane, or paraffins, alcohols and glycols and their ethers and esters, such as ethanol, ethylene glycol, ethylene glycol monomethyl or monoethyl ether; ketones such as cyclohexanone, strongly polar solvents such as N-methyl-2-pyrrolidone, dimethyl sulfoxide or dimethyl formamide; as well as epoxidised vegetable oils such as epoxidised coconut oil or soybean oil; or water. The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali, alkaline earth or unsubstituted or substituted ammonium salts of higher fatty acids (C$_{10}$-C$_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali, alkaline earth or unsubstituted or substituted ammonium salts and contain a C$_8$-C$_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 glycol units per propylene glycol unit.

Representative examples of non-ionic surfactants are nonylphenol-polyethoxyethanols, castor oil polyglycol ehters, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp. Ringwood, N.J., 1979; Sisely and Wood, "Encyclopedia of Surface Active Agents", Chemical Publishing Co. Inc., New York, 1964.

The pesticidal formulations will normally contain 0.1 to 99%, preferably 0.1 to 95%, of a compound of the formula I, 1 to 99% of a solid or liquid adjuvant, and 0 to 25%, preferably 0.1 to 25%, of a surfactant.

Whereas commercial products will be preferably formulated as concentrates, the end user will normally employ dilute formulations.

The compositions can also contain further ingredients such as stabilisiers, antifoams, viscosity regulators, binders, adhesives, as well as fertilisers or other active compounds, in order to attain special effects.

In the following Examples parts and percentages are by weight.

PREPARATORY EXAMPLES

EXAMPLE 1

2-p-Tolyl-4,6-bis-isopropoxypyrimidine

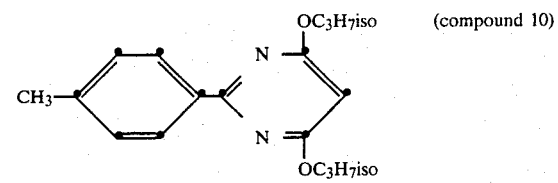

(compound 10)

(a) 21.16 g of sodium are dissolved in anhydrous isopropanol and to this solution are added 95.64 g of 4,6-dichloro-2-p-tolylpyrimidine at 60°–65° C. over 15 minutes. The mixture is then heated to the boil and refluxed for a further 4 hours to bring the reaction to completion. Excess isopropanol is then distilled off and the residual oil is taken up in chloroform. The chloroform layer is washed with water, dried over sodium sulfate, and filtered. The solvent is then distilled off, affording 112 g of 2-p-tolyl-4,6-bis-isopropoxypyrimidine in the form of a yellowish oil which is purified by high vacuum distillation. The boiling point is 123° C./5.332 Pascal.

The starting 2-p-tolyl-4,6-dichloropyrimidine is prepared as follows:

(b) 102.3 g of p-tolylamidine hydrochloride and 99.3 g of diethyl malonate are suspended in 520 ml of anhydrous ethanol. With good stirring and cooling, 323.7 g of a 30% solution of sodium methylate are then run in. The reaction mixture is then heated to reflux and stirring at reflux temperature for 5 hours. The solvent is then distilled off and the residue is taken up in 1000 ml of water, heated to 80° C., and the somewhat turbid solution is then filtered over silica gel. The filtrate is cooled and acidified with 15% hydrochloric acid. The dense crystalline slurry is filtered and the filter residue is washed with water and dried at 100° C., affording 100–110 g of 2-p-tolyl-4,6-dihydroxypyrimidine with a melting point of 314° C. (with decompos.).

(c) 72.6 g of the dihydroxy compound, 72.6 g of N,N-dimethylaniline and 363 g of phosphoroxy chloride are heated to the boil and the mixture is stirred at reflux for 1 hour. Excess phosphoroxy chloride is distilled off and then the residue is washed with iced water to remove any phosphoroxy chloride still remaining, triturated with iced water, and filtered. The filter residue is washed with iced water and vacuum dried at 40°–50° C., affording 85.9 g of 2-p-tolyl-4,6-dichloropyrimidine with a melting point of 86°–87° C.

EXAMPLE 2

2-p-Tolyl-4,6-bis-isopropoxy-5-bromopyrimidine

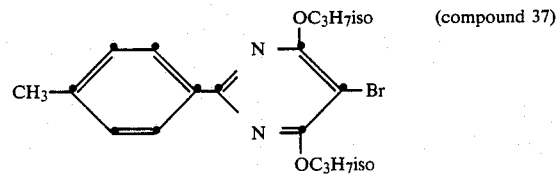

(compound 37)

111.7 g of 4,6-diisopropoxy-2-p-tolylpyrimidine and 450 ml of carbon tetrachloride are heated to 70°–75° C. To the resultant solution is added 0.5 g of dibenzoyl peroxide, followed by the addition, over 45 minutes, of a mixture of 1 g of azoisobutyronitrile and 70.8 g of N-bromosuccinimide. The mixture is refluxed for 2 hours to bring the reaction to completion. The precipitated succinimide is then filtered off and excess carbon tetrachloride is removed by distillation, affording 141 g of the title compound with a melting point of 74°–75° C. after purification with methanol.

EXAMPLE 3

2-p-Tolyl-4,6-dimethoxypyrimidine

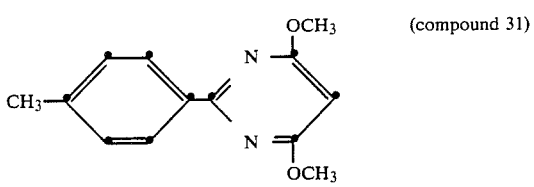

(compound 31)

156.1 g of a 30.5% solution of sodium methylate are stirred with 700 ml of anhydrous methanol. To the solution are then added, over 10 minutes and with gentle cooling, 95.64 g of 2-p-tolyl-4,6-dichloropyrimidine. The mixture is then heated to reflux and kept at the boil for 4 hours. The solvent is removed by distillation and the residue is charged into 1000 ml of water. The product is triturated with water to remove sodium chloride, isolated by filtration, washed with water and dried in the air, affording 90.4 g of the title compound with a melting point of 61°–62° C.

EXAMPLE 4

2-p-Chlorophenyl-4,6-dihydroxypyrimidine

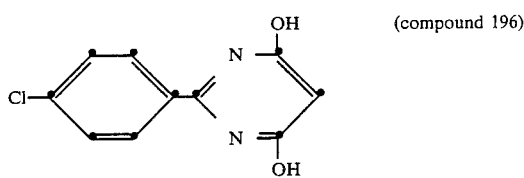

(compound 196)

108 g of a 30% solution of sodium methylate in methanol are added over 10 minutes to a suspension of 38.2 g of 4-chlorobenzyllamidine hydrochloride and 33.6 g of diethyl malonate in 175 ml of methanol, and the mixture is subsequently refluxed for 5 hours. The solvent is then distilled off in a rotary evaporator and the residue is taken up in 1000 ml of hot water and the solution is filtered. The filtrate is then acidified to pH 1 and the precipitate is isolated by filtration and vacuum dried at 80° C., affording 44 g of 2-p-chlorophenyl-4,6-dihydroxypyrimidine with a melting point of 333° C. (decompos.).

EXAMPLE 5

2-p-Chlorophenyl-4,6-dichloropyrimidine

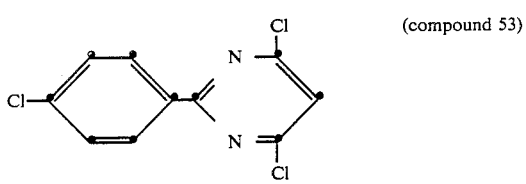

(compound 53)

50 ml of phosphoroxy chloride (POCl₃) are added dropwise at room temperature to 22 ml of N,N-dimethyl aniline. Then 22.3 g of 2-p-chlorophenyl-4,6-dihydroxypyrimidine are added in portions with cooling, such that the temperature remains below 40° C. The reaction mixture is stirred for 2 hours at room temperature, then refluxed for 2 hours, and subsequently concentrated by rotary evaporation. The residue is triturated with 500 ml of water and filtered with suction. The filter cake is dissolved in methylene chloride and the solution is treated with fuller's earth, dried and concentrated. The residue crystallises, giving 16.2 g of 2-p-chlorophenyl-4,6-dichloropyrimidine with a melting point of 119°–120° C. A sample sublimed at 80°/0.02 mbar melts at 120°–121° C.

EXAMPLE 6

2-p-Methoxyphenyl-4,6-dihydroxypyrimidine

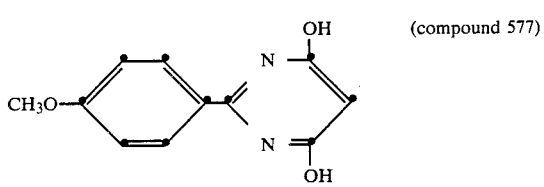

(compound 577)

338 g of a 30% solution of sodium methylate in methanol are added over 10 minutes to a suspension of 112 g of p-methoxybenzamidine hydrochloride and 101 g of diethyl malonate in 520 ml of ethanol, and the mixture is subsequently refluxed for 5 hours. The reaction mixture is then concentrated by rotary evaporation and the residue is dissolved in 1000 ml of warm water of 80° C. The solution is filtered and the filtrate is acidified to pH 1. The precipitate is isolated by filtration and vacuum dried at 80° C., affording 109.8 g of 2-p-methoxyphenyl-4,6-dihydroxypyrimidine with a melting point of 318° C. (decompos.).

EXAMPLE 7

2-p-Methoxyphenyl-4,6-dichloropyrimidine

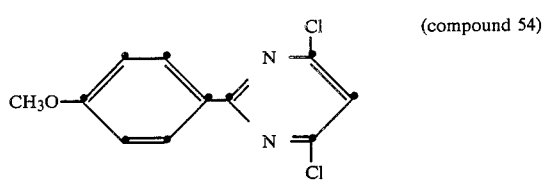

(compound 54)

126 ml of phosphoroxy chloride (POCl₃) and then 57 ml of N,N-dimethyl aniline are added dropwise over 30 minutes to 54.5 g of 2-p-methoxyphenyl-4,6-dihydroxypyrimidine with cooling, such that the temperature does not exceed 45° C. The reaction mixture is then stirred for 2 hours at room temperature and subsequently refluxed for 2 hours. The reaction mixture is then concentrated by rotary evaporation and the residue is triturated in 2 liters of iced water. The solid product is isolated by filtration, dissolved in 1.5 liters of methylene chloride and the solution is treated with fuller's earth and dried. The methylene chloride solution is filtered and concentrated. The residue is recrystallised from ethanol, affording 51 g of crystalline 2-p-methoxyphenyl-4,6-dichloropyrimidine with a melting point of 127°–128° C.

The following compounds are prepared by procedures similar to those described in the preceding Examples:

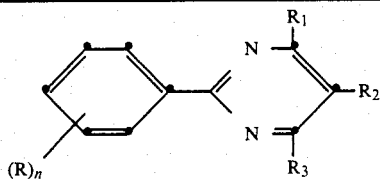

| No. | (R)$_n$ | R$_1$ | R$_2$ | R$_3$ | Physical data (°C.) |
|---|---|---|---|---|---|
| 1 | (H)$_5$ | Cl | H | Cl | m.p. 95–96° |
| 2 | 4-CH$_3$ | Cl | H | Cl | m.p. 86–87° |
| 3 | 4-CH$_3$ | Cl | CH$_3$ | Cl | m.p. 153–154° |
| 4 | 4-CH$_3$ | Cl | phenyl | Cl | m.p. 132–133° |
| 5 | (H)$_5$ | Cl | H | CH$_3$ | m.p. 71–72° |
| 6 | 4-CH$_3$ | Cl | H | CH$_3$ | m.p. 103–104° |
| 7 | 4-CH$_3$ | Cl | H | OH | m.p. 229–234° |
| 8 | 4-CH$_3$ | Cl | H | OCH$_3$ | m.p. 92–93° |
| 9 | 4-CH$_3$ | Cl | CH$_3$ | OCH$_3$ | m.p. 143–144° |
| 10 | 4-CH$_3$ | Cl | H | OC$_3$H$_7$iso | m.p. 55–57° |
| 11 | 4-CH$_3$ | Cl | H | 4-methylphenyl | m.p. 86–87° |
| 12 | 4-CH$_3$ | Cl | H | 4-methoxyphenyl | m.p. 102–104° |
| 13 | 4-CH$_3$ | Cl | H | NHCH$_3$ | m.p. 107° |
| 14 | 4-CH$_3$ | Cl | Br | NHCH$_3$ | m.p. 105–107° |
| 15 | 4-CH$_3$ | Cl | H | N(C$_2$H$_5$)$_2$ | m.p. 74–75° |
| 16 | (H)$_5$ | CH$_3$ | H | OH | oil |
| 17 | 4-CH$_3$ | CH$_3$ | H | OH | m.p. 206–207° |
| 18 | (H)$_5$ | CH$_3$ | H | OCH$_3$ | b.p.156–8°/1.33·10$^3$ pa |
| 19 | 4-CH$_3$ | CH$_3$ | H | OCH$_3$ | m.p. 66–67° |
| 20 | 4-CH$_3$ | CH$_3$ | H | 4-methoxyphenyl | m.p. 90–91° |
| 21 | (H)$_5$ | CH$_3$ | H | OC$_2$H$_4$OCH$_3$ | b.p. 158–160°/13.33 pa |
| 22 | (H)$_5$ | CH$_3$ | H | (OC$_2$H$_4$)$_2$OCH$_3$ | b.p. 148–150°/2.66 pa |
| 23 | 4-CH$_3$ | CH$_3$ | H | OC$_2$H$_4$OCH$_3$ | m.p. 61–62° |
| 24 | (H)$_5$ | CH$_3$ | H | N(CH$_3$)$_2$ | m.p. 55–57° |
| 25 | 4-CH$_3$ | CH$_3$ | H | N(CH$_3$)$_2$ | m.p. 97–98° |
| 26 | 4-CH$_3$ | CH$_3$ | Br | N(CH$_3$)$_2$ | m.p. 49–50° |
| 27 | (H)$_5$ | CH$_3$ | H | morpholino | m.p. 88–90° |
| 28 | 4-CH$_3$ | CH$_3$ | H | morpholino | m.p. 123–124° |
| 29 | 4-CH$_3$ | CH$_3$ | Br | morpholino | m.p. 113–114° |
| 30 | 4-CH$_3$ | OCH$_3$ | H | 4-methylphenyl | m.p. 99–100° |
| 31 | 4-CH$_3$ | OCH$_3$ | H | OCH$_3$ | m.p. 61–62° |
| 32 | 4-CH$_3$ | OCH$_3$ | CH$_3$ | OCH$_3$ | m.p. 93–94° |
| 33 | 4-CH$_3$ | OCH$_3$ | 4-methylphenyl | OCH$_3$ | m.p. 214° |
| 34 | 4-CH$_3$ | OC$_2$H$_5$ | H | OC$_2$H$_5$ | m.p. 71° |

-continued

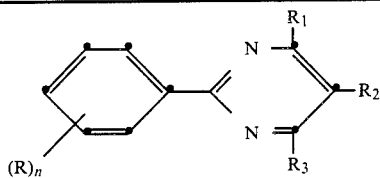

| No. | (R)$_n$ | R$_1$ | R$_2$ | R$_3$ | Physical data (°C.) |
|---|---|---|---|---|---|
| 35 | 4-CH$_3$ | OC$_3$H$_7$n | H | OC$_3$H$_7$iso | m.p. 62° |
| 36 | 4-CH$_3$ | OC$_3$H$_7$iso | H | OC$_3$H$_7$iso | b.p. 123°/5.332 Pa Example 1 |
| 37 | 4-CH$_3$ | OC$_3$H$_7$iso | Br | OC$_3$H$_7$iso | m.p. 73–74° Example 2 |
| 38 | 4-CH$_3$ | OC$_4$H$_9$n | H | OC$_4$H$_9$n | b.p. 158–161°/13.332 Pa |
| 39 | 4-CH$_3$ | O—C$_6$H$_5$ | H | O—C$_6$H$_5$ | m.p. 125–126° |
| 40 | 4-CH$_3$ | SC$_2$H$_5$ | H | SC$_2$H$_5$ | m.p. 55–56° |
| 41 | 4-CH$_3$ | OC$_2$H$_4$OCH$_3$ | H | OC$_2$H$_4$OCH$_3$ | oil |
| 42 | 4-CH$_3$ | OC$_2$H$_4$OCH$_3$ | CH$_3$ | OC$_2$H$_4$OCH$_3$ | oil |
| 43 | 4-CH$_3$ | OC$_2$H$_4$OCH$_3$ | Cl | OC$_2$H$_4$OCH$_3$ | m.p. 55–57° |
| 44 | 4-CH$_3$ | OC$_2$H$_4$OCH$_3$ | Br | OC$_2$H$_4$OCH$_3$ | m.p. 55–56° |
| 45 | 4-CH$_3$ | OC$_2$H$_4$OCH$_3$ | H | NHCH$_3$ | m.p. 65–66° |
| 46 | 4-CH$_3$ | OC$_2$H$_4$OCH$_3$ | Br | NHCH$_3$ | oil |
| 47 | 4-CH$_3$ | OC$_2$H$_4$OCH$_3$ | H | N(C$_2$H$_5$)$_2$ | oil |
| 48 | 4-CH$_3$ | —N(morpholino) | H | —N(morpholino) | m.p. 125–126° |
| 49 | 4-CH$_3$ | Br | H | Br | m.p. 125–126° |
| 50 | (H)$_5$ | Br | H | Br | m.p. 115–118° |
| 51 | (H)$_5$ | Cl | H | OH | m.p. 218–221° |
| 52 | (H)$_5$ | Cl | H | SH | m.p. 150° Z |
| 53 | 4-Cl | Cl | H | Cl | m.p. 120° |
| 54 | 4-OCH$_3$ | Cl | H | Cl | m.p. 127–128° |
| 55 | 4-CN | Cl | H | Cl | m.p. 230–232° |
| 56 | 3-CF$_3$ | Cl | H | Cl | m.p. 56–57° |
| 57 | 2-CH$_3$ | Cl | H | Cl | m.p. 74–75° |
| 58 | 2-CH$_3$ | Cl | Cl | Cl | m.p. 122–125° |
| 59 | 3-Cl, 4-F | Cl | H | Cl | m.p. 94–95° |
| 60 | 2,6(CH$_3$)$_2$ | Cl | H | Cl | m.p. 103–104° |
| 61 | 3,4(CH$_3$)$_2$ | Br | H | Br |  |
| 62 | 4-C$_3$H$_7$i | Cl | H | Cl | m.p. 63–64° |
| 63 | 4-C$_3$H$_7$i | Cl | H | F |  |
| 64 | 4-Cl | F | H | F | m.p. 139–141° |
| 65 | 2-CH$_3$, 6-C$_2$H$_5$ | Cl | H | Cl |  |
| 66 | 2-CH$_3$, 6-C$_2$H$_5$ | Cl | H | C$_2$H$_5$ |  |
| 67 | 2-Cl | Cl | H | Cl | m.p. 116–118° |
| 68 | 3-C$_2$H$_5$ | Cl | H | Cl |  |
| 69 | 4-CH$_3$ | Cl | F | Cl |  |
| 70 | 4-F | Cl | F | Cl |  |
| 71 | 3-CHF$_2$ | Cl | H | Cl |  |
| 72 | 2, 4(CH$_3$)$_2$ | Br | H | Br |  |
| 73 | 2,3,6(CH$_3$)$_3$ | Cl | H | Cl |  |
| 74 | 3-C$_3$H$_7$i | Cl | H | Cl |  |
| 75 | 4-CHF$_2$ | Cl | H | Cl |  |
| 76 | 2-Cl, 4-CH$_3$ | Br | H | Br |  |
| 77 | 3,4(Cl)$_2$ | Cl | H | Cl | OH |
| 78 | 4-OCH$_2$CH=CH$_2$ | Cl | H | Cl | m.p. 57–58° |
| 79 | 4-OH | F | H | F |  |
| 80 | 4-COCH$_3$ | Cl | H | Cl | m.p. 129–130° |
| 81 | 4-OCOC$_2$H$_5$ | Cl | H | Cl |  |
| 82 | 4-OCH(CH$_3$)COOCH$_3$ | Cl | H | Cl |  |
| 83 | 4-OCF$_2$Cl | Cl | H | OC$_2$H$_5$ |  |
| 84 | 4-OH | Cl | H | Cl | m.p. 135–137° |
| 85 | 4-OCON(CH$_3$)$_2$ | Cl | H | Cl | m.p. 191–193° |
| 86 | 3-CH$_2$F | Cl | H | Cl |  |
| 87 | 2-COOCH$_3$ | Cl | H | OC$_4$H$_9$n |  |
| 88 | 4-CH$_2$F | Cl | H | Cl |  |
| 89 | 4-COOCH$_3$ | Cl | H | Cl | m.p. 135–140° |
| 90 | 4-COOC$_4$H$_9$n | Cl | H | OC$_4$H$_9$n |  |
| 91 | 4-Cl, 2,6(OCH$_3$)$_2$ | Cl | H | Cl |  |
| 92 | 4-CHO | Cl | H | Cl | m.p. 160–162° |
| 93 | 3-CH$_2$Cl | Cl | H | Cl |  |
| 94 | 3,5(CF$_3$)$_2$ | Cl | H | Cl |  |
| 95 | 4-CF$_3$ | Br | H | Br |  |
| 96 | 4-OCHF$_2$ | Cl | H | Cl |  |
| 97 | 3,5(OC$_2$H$_5$)$_2$ | Cl | H | Cl |  |

-continued

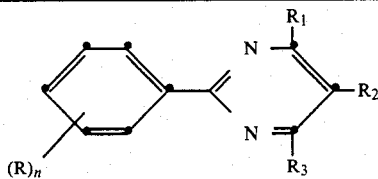

| No. | (R)$_n$ | R$_1$ | R$_2$ | R$_3$ | Physical data (°C.) |
|---|---|---|---|---|---|
| 98 | 4-OC$_3$H$_7$i | F | H | F | |
| 99 | 3-NO$_2$ | Cl | H | Cl | m.p. 136–138° |
| 100 | 4-NO$_2$ | Cl | H | Cl | m.p. 167–168° |
| 101 | 3-NO$_2$, 4-CH$_3$ | Cl | H | Cl | |
| 102 | 2-Cl, 4-NO$_2$ | Cl | H | Cl | |
| 103 | 2-N(CH$_3$)$_2$ | Cl | H | Cl | |
| 104 | 3-NHCOCH$_3$ | Br | H | Br | |
| 105 | 3-NHCOCH$_2$Cl | Cl | H | Cl | |
| 106 | 4-OCF$_3$ | Cl | H | OC$_3$H$_7$i | |
| 107 | 3-OCF$_2$Cl, 5-Cl | Cl | H | Cl | |
| 108 | 2-CON(CH$_3$)$_2$ | Cl | H | Cl | |
| 109 | 4-OCF$_2$CHF$_2$ | Cl | H | Cl | |
| 110 | 4-CONHC$_4$H$_9$n | Cl | H | Cl | |
| 111 | 4-NHCOCH$_2$Cl | Cl | H | Cl | m.p. 196–198° |
| 112 | 4-COCH$_3$, 3-CH$_3$ | Cl | H | CH$_3$ | |
| 113 | 3-CH$_2$—COCH$_3$ | F | H | OCH$_3$ | |
| 114 | 4-COC$_3$H$_7$n | Cl | H | Cl | |
| 115 | 4-OCF$_2$CHFCl | Cl | H | Cl | |
| 116 | 2-OH | Cl | H | Cl | |
| 117 | 4-COOCH$_2$CH=CH$_2$ | Cl | H | Cl | |
| 118 | 4-COOCH$_2$C≡CH | Cl | H | Cl | m.p. 105–109° |
| 119 | 2-Cl, 6-C≡CH | Cl | H | Cl | |
| 120 | 3-C≡C—C(CH$_3$)$_2$OCH$_3$ | Br | H | Br | |
| 121 | 4-C≡C—C(CH$_3$)$_2$OH | Cl | H | Cl | |
| 122 | 4-C≡C—C(CH$_3$)$_2$OCH$_3$ | Cl | H | Cl | |
| 123 | 3,5(I)$_2$, 4-OCH(CH$_3$)COOCH$_3$ | Cl | H | Cl | |
| 124 | (H)$_5$ | Cl | CF$_3$ | Cl | |
| 125 | 4-CH=CH—C$_4$H$_9$n | Cl | H | Cl | |
| 126 | 4Cl$_3$ | Cl | CF$_3$ | Cl | |
| 127 | 4-OH | Br | H | Br | |
| 128 | 4-Br | Cl | H | Cl | m.p. 130–131° |
| 129 | 3-OH | Cl | H | Cl | m.p. 144–146° |
| 130 | 3-OCH$_3$ | Cl | H | Cl | m.p. 97–100° |
| 131 | 3-OCOCH$_2$Cl | Cl | H | Cl | |
| 132 | 2-OCH$_3$ | Cl | H | Cl | m.p. 67–70° |
| 133 | 2,6(F)$_2$ | Cl | H | Cl | m.p. 102–105° |
| 134 | 4-F | Cl | H | Cl | m.p. 91–92° |
| 135 | 3-Cl, 4-CH$_3$ | Cl | H | Cl | |
| 136 | (H)$_5$ | F | H | F | m.p. 114–116° |
| 137 | (H)$_5$ | F | H | Cl | m.p. 105° |
| 138 | 2,5(Cl)$_2$, 4-OH | F | H | F | |
| 139 | 2-Cl, 4-OCH(CH$_3$)COOC$_2$H$_5$ | Cl | H | Cl | |
| 140 | 2,3,5(Cl)$_3$, 4-OH | Cl | H | Cl | |
| 141 | 2,3,5(Cl)$_3$, 4-OC$_2$H$_5$ | Cl | H | Cl | |
| 142 | 2,3,5,6(CH$_3$)$_4$, 4-NO$_2$ | Cl | H | Cl | |
| 143 | (H)$_5$ | F | CF$_3$ | Cl | |
| 144 | 3-SO$_2$N(CH$_3$)$_2$ | Cl | H | Cl | |
| 145 | 4-CSN(CH$_3$)$_2$ | Cl | H | Cl | |
| 146 | 4-C(CH$_3$)=CH$_2$ | Cl | H | Cl | |
| 147 | 4-CH$_2$COOCH$_3$ | Cl | H | Cl | |
| 148 | 4-CH$_2$PO(OC$_2$H$_5$)$_2$ | Cl | H | Cl | |
| 149 | 4-CH$_2$PO(OH)$_2$ | Br | H | Br | |
| 150 | 4-SO$_2$N(CH$_3$)$_2$, 5-CH$_3$ | Cl | H | OC$_4$H$_9$n | |
| 151 | 4-PO(OH)$_2$ | Br | H | Br | |
| 152 | 4-PO(OCH$_3$)$_2$ | Cl | H | Cl | |
| 153 | 3-PO(OCH$_3$)$_2$ | Cl | H | Cl | |
| 154 | H | SOCH$_3$ | H | Cl | |
| 155 | 4-CH$_2$CH=CH$_2$ | Cl | H | Cl | |
| 156 | 3-C≡CH, 5-CH$_3$ | Cl | H | Cl | |
| 157 | 2-C≡CH | Cl | H | Cl | |
| 158 | 4-C≡CH | Cl | H | Cl | m.p. 168–170° |
| 159 | H | SOCH$_3$ | H | Br | |
| 160 | 4-C(OCH$_3$)$_2$C$_3$H$_7$n | Cl | H | OCH$_3$ | |
| 161 | 2-CH$_3$, 5-N(CH$_3$)$_2$ | Cl | H | Cl | |
| 162 | 2-CH$_3$, 5-Cl | Cl | H | Cl | |
| 163 | 3-Br, 4-OH | Cl | H | OCH$_2$CH=CH$_2$ | |
| 164 | 3-Br, 4-OC$_3$H$_7$n | Cl | H | Cl | |
| 165 | 3-NO$_2$4-Cl | Cl | H | Cl | m.p. 158–159° |
| 166 | 3-NH$_2$, 4-Cl | Cl | H | Cl | |
| 167 | 3-CH$_3$, 4-NO$_2$ | Cl | H | Cl | m.p. 173–175° |
| 168 | 3-CH$_3$, 4-NH$_2$ | Cl | H | Cl | solid |
| 169 | 3-CH$_3$, 4-NHCON(CH$_3$)$_2$ | F | H | OCH$_2$CH=CH$_2$ | |

-continued

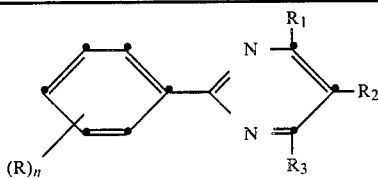

| No. | (R)n | R1 | R2 | R3 | Physical data (°C.) |
|---|---|---|---|---|---|
| 170 | 2-Cl, 5-CF3 | Cl | H | Cl | |
| 171 | 3-CF3, 4-Cl | Cl | H | Cl | |
| 172 | 4-CH3 | SOCH3 | H | Cl | |
| 173 | 2-Cl, 5-N(CH3)2 | Cl | H | OH | |
| 174 | 2,6(OCH3)2, 3-NO2 | Cl | H | Cl | |
| 175 | 2,6(OCH3)2, 3-NH2 | Cl | H | Cl | |
| 176 | 2,6(OCH3)2, 3-NHCOCH3 | Cl | H | Cl | |
| 177 | 2-CH3, 6-C2H5, 4-OCON(CH3)2 | Cl | H | Cl | |
| 178 | 3,5(I)2, 4-OH | Cl | H | Cl | |
| 179 | 3,5(I)2, 4-OCH3 | Br | H | Br | |
| 180 | 3,5(Br)2, 4-OH | Cl | H | Cl | |
| 181 | 3,5(Br)2, 4-OCH2—CH=CH2 | Cl | H | Cl | |
| 182 | 3,4,5(OCH3)3 | Cl | H | Cl | m.p. 167–169° |
| 183 | 2,3(Cl)2 | Cl | H | Cl | m.p. 116–118° |
| 184 | 4-CH3 | F | H | SOCH3 | |
| 185 | (H)5 | SOCH3 | H | CN | |
| 186 | (H)5 | SCH3 | H | CN | |
| 187 | (H)5 | SO2CH3 | H | CN | |
| 188 | (H)5 | —O—CO—CH3 | H | Cl | |
| 189 | 4-CH3 | CN | Cl | Cl | |
| 190 | 3-SO2NHCOONC3H7(i) | Cl | H | Cl | |
| 191 | 4-⟨cyclopentyl⟩ | Cl | H | Cl | |
| 192 | 3-⟨cyclopropyl⟩ | Br | H | Br | |
| 193 | 3-⟨cyclohexenyl⟩ | Cl | H | Cl | |
| 194 | 3-CH2—C(CH3)(O)(O) (dioxolane) | F | H | OCH3 | |
| 195 | 3-CF3 | OH | H | OH | m.p. 286° C. |
| 196 | 4-CH3 | OCH3 | H | OH | |
| 197 | 3-NH2 | Cl | H | Cl | solid |
| 198 | 4-NH2 | Cl | H | Cl | solid |
| 199 | 3-NHCOCH3 | Cl | H | Cl | m.p. 228–230° |
| 200 | 4-NHCOCH3 | Cl | H | Cl | m.p. 190–192° |
| 201 | 4-SO2NHCOOCH3 | Cl | H | Cl | |
| 202 | 3-SO2NCH3COOCH3 | Cl | H | Cl | |
| 203 | 4-CH3,3-SO2H | Cl | H | Cl | |
| 204 | 4-CH3,3-SO2NH2 | Cl | H | Cl | |
| 205 | 4-NHCONHC2H5 | Cl | H | Cl | |
| 206 | 4-Cl, 3-NH2 | Cl | H | Br | |
| 207 | 3-I | Cl | H | Cl | |
| 208 | 3-COOH | Cl | H | Cl | m.p. 250° |
| 209 | 4-COOH | Cl | H | Cl | m.p. 236–238° |
| 210 | 3-CH3 | Cl | H | OH | m.p. 195–200° |
| 211 | 4-N(CH3)2 | Cl | H | Cl | m.p. 150–155° |
| 212 | 3NHCH3 | Cl | H | Cl | |
| 213 | HNHCH3 | | | | |
| 214 | 3-NHCHO | | | | |
| 215 | 4-NHCHO | | | | |
| 216 | 3-NHCO-⟨cyclopropyl⟩ | Cl | H | Cl | |
| 217 | 4-OCH2OCH3 | Cl | H | Cl | |
| 218 | 4-SCH3 | Cl | H | F | |

-continued

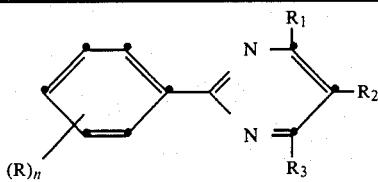

| No. | (R)$_n$ | R$_1$ | R$_2$ | R$_3$ | Physical data (°C.) |
|---|---|---|---|---|---|
| 219 | 3-SH | Cl | H | Cl | |
| 220 | 4-SCH$_3$ | Cl | H | Cl | m.p. 109–111° |
| 221 | 4-OCOOCH$_3$ | Cl | H | F | |
| 222 | 3-OCOOCH$_3$ | Cl | H | Cl | |
| 223 | 3-F | Cl | H | Cl | m.p. 72–74° |
| 224 | 4-OC$_2$H$_4$OC$_2$H$_5$ | Cl | H | Cl | m.p. 75–77° |
| 225 | 4-OC$_2$H$_4$OC$_3$H$_{7n}$ | Cl | H | Cl | wax |
| 226 | 4-CH$_2$—CCl=CH$_2$ | CH$_3$ | H | Cl | |
| 227 | 4-SO$_2$CH$_3$ | Cl | H | Cl | m.p. 163–165° |
| 228 | 4-OC$_2$H$_4$OC$_2$H$_4$OC$_2$H$_5$ | Cl | H | Cl | m.p. 42–43° |
| 229 | 4-OCH$_3$ | Br | H | Br | m.p. 129–131° |
| 230 | —OC$_6$H$_{13n}$ | Cl | H | Cl | |
| 231 | 4-OCH$_2$—C≡CH | Cl | H | Cl | |
| 232 | 4-OC$_2$H$_4$N(C$_2$H$_5$)$_2$ | Cl | H | Cl | |
| 233 | 4-OC$_2$H$_4$Cl | Cl | H | Cl | |
| 234 | 4-OC$_2$H$_4$OH | Cl | H | Cl | |
| 235 | 4-OC$_2$H$_4$SCH$_3$ | Cl | H | Cl | |
| 236 | 4-OC$_2$H$_4$OC$_2$H$_4$Cl | Cl | H | Cl | m.p. 88–89° |
| 237 | 4-OCF$_3$ | Cl | H | Cl | |
| 238 | 4-OC$_2$H$_5$ | Cl | H | Cl | |
| 239 | 4-OCOCH$_3$ | Cl | H | Cl | m.p. 113–115° |
| 240 | 4-OCH(CH$_3$)COOCH$_3$ | Cl | H | Cl | |
| 241 | 4-OCH(CH$_3$)COOCH$_3$ | Br | H | Cl | m.p. 118–120° |
| 242 | 4-OCOCH=CH$_2$ | Cl | H | Cl | |
| 243 | 4-OCOC$_3$H$_6$CH=CH$_2$ | Cl | H | Cl | |
| 244 | 4-OCH$_2$CON(CH$_3$)$_2$ | Cl | H | Cl | |
| 245 | 4-OCH$_2$CH=CHCH$_3$ | Cl | H | Cl | |
| 246 | 4-OC$_2$H$_4$CH=CClCH$_3$ | Cl | H | Cl | |
| 247 | (H)$_5$ | Cl | CHF$_2$ | Cl | |
| 248 | (H)$_5$ | Cl | H | F | |
| 249 | (H)$_5$ | Cl | H | Br | |
| 250 | (H)$_5$ | I | H | I | |
| 251 | 4-SOCH$_3$ | Cl | H | Cl | |
| 252 | 4-SC$_2$H$_4$N(CH$_3$)$_2$ | Cl | H | Cl | |
| 253 | 4-SC$_2$H$_4$OCH$_3$ | Cl | H | Cl | |
| 254 | 4-SC$_6$H$_{13n}$ | Cl | H | Cl | |
| 255 | 4-SC$_2$H$_4$COOC$_4$H$_9$ | Cl | H | Cl | |
| 256 | 4-SCOCH$_3$ | Cl | H | Cl | |
| 257 | 4-SCH$_2$CH=CH$_2$ | Cl | H | Cl | |
| 258 | 4-NH$_2$ | Br | H | Br | |
| 259 | 4-NHC$_6$H$_{13n}$ | Cl | H | Cl | |
| 260 | 4-NHC$_3$H$_{7i}$ | Cl | H | Cl | |
| 261 | 4-NHCH$_2$COOCH$_3$ | Cl | H | Br | |
| 262 | 4-NHCH(CH$_3$)CON(CH$_3$)$_2$ | Cl | H | Cl | |
| 263 | 4-NHCOCH=CH$_2$ | Cl | H | Cl | |
| 264 | 4-NHCH$_2$—CH=CH$_2$ | Cl | H | Cl | |
| 265 | 4-N(CH$_2$—CH=CH$_2$)$_2$ | Cl | H | Cl | |
| 266 | 4-NHCH—C≡CH | Cl | H | Cl | |
| 267 | 4-NHCH$_2$CH=CHC$_2$H$_5$ | Cl | H | Cl | |
| 268 | 4-NH(CH$_2$)$_4$C≡CH | Cl | H | Cl | |
| 269 | 4-NHOCH$_3$ | Cl | H | Cl | |
| 270 | 4-NHOCH$_2$CH=CH$_2$ | Cl | H | Cl | |
| 271 | 4-N(CH$_3$)OCH$_3$ | Cl | H | Cl | |
| 272 | 4-N(CH$_3$)COCH$_3$ | Cl | H | Cl | |
| 273 | 4-B(OCH$_3$)COCH$_3$ | Cl | H | Cl | |
| 274 | 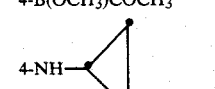 | Cl | H | Cl | |
| 275 | 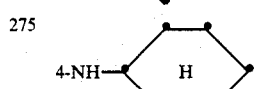 | Cl | H | Cl | |
| 276 | 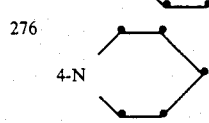 | Cl | H | Cl | |

-continued

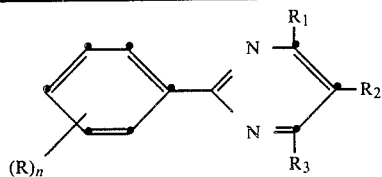

| No. | (R)$_n$ | R$_1$ | R$_2$ | R$_3$ | Physical data (°C.) |
|---|---|---|---|---|---|
| 277 | 4-N(pyrrolidinyl) | Cl | H | Cl | |
| 278 | 4-N(morpholinyl) | Br | H | Br | |
| 279 | 4-N(thiomorpholinyl) | Cl | H | Cl | |
| 280 | 4-N(N'-methylpiperazinyl) | Cl | H | F | |
| 281 | 4-NHCOOCH$_3$ | Cl | H | Cl | |
| 282 | 4-N(CH$_3$)COOC$_3$H$_{7i}$ | Cl | H | Cl | |
| 283 | 4-NHCONHCH$_3$ | Cl | H | Cl | |
| 284 | 4-NHCON(CH$_3$)$_2$ | Cl | H | Cl | |
| 285 | 4-N(CH$_3$)CONHCH$_3$ | Cl | H | Cl | |
| 286 | 4-N(CH$_3$)CON(CH$_3$)OCH$_3$ | Cl | H | Cl | |
| 287 | COOC$_6$H$_{13}$n | Cl | H | Cl | |
| 288 | 4-OCOCH$_2$CH=CHCH$_3$ | Cl | H | Cl | |
| 289 | 4-CONH$_2$ | Cl | H | Cl | |
| 290 | 4-CON(C$_3$H$_7$n)$_2$ | Cl | H | Cl | |
| 291 | 4-CONHC$_6$H$_{13}$n | Cl | H | Cl | |
| 292 | 4-OCOC$_2$H$_4$N(C$_2$H$_5$)$_2$ | Br | H | Br | |
| 293 | 4-CONHOCH$_3$ | Cl | H | Cl | |
| 294 | 4-CON(CH$_3$)$_2$ | Cl | H | Cl | |
| 295 | 4-CHO | Br | H | Br | |
| 296 | 4-COC$_4$H$_9$n | Cl | H | Cl | |
| 297 | 4-COCH=CH—N(CH$_3$)$_2$ | Cl | H | Cl | |
| 298 | 4-CSN(C$_3$H$_7$)$_2$ | Cl | H | Cl | |
| 299 | 4-CSNHC$_6$H$_{13}$n | Cl | H | Cl | |
| 300 | 4-N=CHC$_3$H$_7i$ | Cl | H | Cl | |
| 301 | 4-N=CHC$_6$H$_{13}$n | Cl | H | Cl | |
| 302 | 4-N=CH(CH$_3$)$_2$ | Cl | H | Cl | |
| 303 | 4-N=(cyclohexylidene) | Cl | H | Cl | |
| 304 | 4-N(CH$_3$)CH$_2$OCH$_3$ | Cl | H | Cl | |
| 305 | 4-SO$_2$NH$_2$ | Cl | H | Cl | |
| 306 | 4-SO$_2$N(CH$_3$)$_2$ | Cl | H | Cl | |
| 307 | 4-SO$_2$NHC$_4$H$_9$ | Cl | H | Cl | |
| 308 | 3-SO$_2$N(pyrrolidinyl) | Br | H | Br | |
| 309 | 4-SO$_2$NHCH$_2$CH=CH$_2$ | Cl | H | Cl | |
| 310 | 4-CH(OCH$_3$)$_2$ | Cl | H | Cl | |
| 311 | 4-CH(OC$_2$H$_4$OCH$_3$)$_2$ | Cl | H | F | |
| 312 | 4-C(C$_4$H$_9$n)(OC$_2$H$_5$)$_2$ | Cl | H | Cl | |
| 313 | 4-C(CH$_3$)(OCH$_3$)$_2$ | Cl | H | Cl | |
| 314 | 4-C(CH$_3$)(OC$_2$H$_4$SCH$_3$)$_2$ | Cl | H | Cl | |
| 315 | 4-CH(dioxolane) | Cl | H | Cl | |

-continued

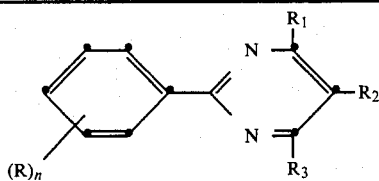

| No. | (R)n | R₁ | R₂ | R₃ | Physical data (°C.) |
|---|---|---|---|---|---|
| 316 | 4-CH(O-CH₂-O-CH₃) (dioxolane with CH₃) | Cl | H | Cl | |
| 317 | 4-C(CH₃)(O-CH₂-O) | Cl | H | Cl | |
| 318 | 4-C(CH₃)(O-CH₂-CH₂-O) | Cl | H | Cl | |
| 319 | 4-PO(OH)OC₂H₅ | Cl | H | Cl | |
| 320 | 4-SO₃H | Cl | H | Cl | |
| 321 | 4-CF₃ | Cl | H | Cl | |
| 322 | 4-CH₂Br | Cl | H | Cl | m.p. 155–156° |
| 323 | 4-CH₂Cl | Cl | H | Cl | |
| 324 | 4-CH₂OCH₃ | Cl | H | Cl | |
| 325 | 4-CH₂OH | Cl | H | Cl | |
| 326 | 4-CH₂OCOCH₃ | Cl | H | Cl | m.p. 108–110° |
| 327 | 4-CH₂OC₄H₉n | Cl | H | Cl | |
| 328 | 4-CH₂SCH₃ | Cl | H | Cl | |
| 329 | 4-CH₂N(CH₃)₂ | Cl | H | Cl | |
| 330 | 4-CHClCH₃ | Cl | H | F | |
| 331 | 4-C₂H₅ | Cl | H | Cl | |
| 332 | 4-C₆H₁₃n | Cl | H | Cl | |
| 333 | 4-C₅H₁₁iso | Br | H | Br | |
| 334 | 4-C≡CCH₃ | Cl | H | Cl | |
| 335 | 4-CH=CH₂ | Cl | H | Cl | |
| 336 | 4-CH₂—CH=CH₂ | Cl | H | F | |
| 337 | 4-CCl=CH₂ | Cl | H | Cl | m.p. 128–130° |
| 338 | 4-C₂H₄Cl | Cl | H | Cl | |
| 339 | 4-C₂H₄N(C₂H₅)₂ | Cl | H | Cl | |
| 340 | 4-cyclohexyl | Cl | H | Cl | |
| 341 | 4-cyclohexenyl | Cl | H | Cl | |
| 342 | 4-cyclopropyl | Cl | H | Cl | |
| 343 | 4-CH=CH₂—CH₂OCH₃ | Cl | H | Cl | |
| 344 | 4-N(CH₃)COCH₂Cl | Cl | H | Cl | |
| 345 | 4-CH₂CN | Cl | H | Cl | m.p. 151–158° |
| 346 | 3-F | Br | H | Br | |
| 347 | 3-Cl | Cl | H | Cl | m.p. 117–119° |
| 348 | 3-NO₂ | Br | H | Br | m.p. 165–167° |
| 349 | 3-NO₂ | F | H | F | |
| 350 | 3-OC₃H₇i | Cl | H | Cl | |
| 351 | 3-OCH₂CH=CHCH₃ | Cl | H | F | |
| 352 | 3-OCH₂C≡CH | Cl | H | Cl | |
| 353 | 3-OC₂H₄N(C₂H₅)₂ | Cl | H | Cl | |
| 354 | 3-OCH(CH₃)CH₂N(C₂H₅) | Cl | H | Cl | |
| 355 | 3-OC₂H₄Cl | Cl | H | Cl | |
| 356 | 4-CH₃ | Br | H | Cl | |
| 357 | 3-OC₂H₄SC₂H₅ | Cl | H | Cl | |
| 358 | 3-OC₂H₄OC₃H₇n | Cl | H | Cl | |
| 359 | 3-OCF₃ | Cl | H | F | |
| 360 | 3-OCHF₂ | Cl | H | Cl | |
| 361 | 3-OCF₂CHF₂ | Cl | H | Cl | |

-continued

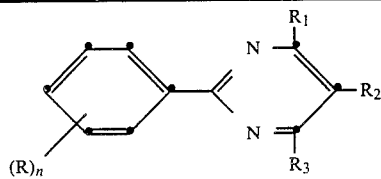

| No. | (R)$_n$ | R$_1$ | R$_2$ | R$_3$ | Physical data (°C.) |
|---|---|---|---|---|---|
| 362 | 3-OCF$_2$CHFCl | Br | H | Br | |
| 363 | 3-OCOC$_2$H$_5$ | Cl | H | Cl | |
| 364 | 3-OCOCH$_2$Cl | Br | H | Br | |
| 365 | 3-SC$_2$H$_5$ | Cl | H | Cl | |
| 366 | 3-SCF$_3$ | Cl | H | Cl | |
| 367 | 3-SCHF$_2$ | Cl | H | Cl | |
| 368 | 3-SO$_2$CH$_3$ | Cl | H | Cl | |
| 369 | 3-SC$_3$H$_6$N(CH$_3$)$_2$ | Cl | H | Cl | |
| 370 | 3-SC$_3$H$_6$Cl | Cl | H | Cl | |
| 371 | 3-SC$_5$H$_{11}$iso | Cl | H | Cl | |
| 372 | 3-SCH$_2$COOC$_3$H$_7$n | Cl | H | F | |
| 373 | 3-S—CH$_2$—C≡CH | Cl | H | Cl | |
| 374 | 3-NH$_2$ | Br | H | Br | solid |
| 375 | 3-N(CH$_3$)$_2$ | Cl | H | Cl | |
| 376 | 3-NHC$_4$H$_9$n | Cl | H | Cl | |
| 377 | 3-NHC$_4$H$_9$sek | Cl | H | Cl | |
| 378 | 3-N(CH$_2$C≡CH)$_2$ | Cl | H | F | |
| 379 | 3-NHCH$_2$CH=CH$_2$ | Cl | H | Cl | |
| 380 | 3-N(CH$_3$)COCH$_2$Cl | Cl | H | Cl | |
| 381 | 3-SO$_2$NHCO$_2$CH$_3$ | Cl | H | Cl | m.p. 160–161° |
| 382 | 3-NHCOCH=CH—CH$_3$ | Cl | H | Cl | |
| 383 | 3-NHOH | Br | H | Br | |
| 384 | 3-NHOC$_2$H$_5$ | Cl | H | Br | |
| 385 | 3-NCH$_3$OCH$_3$ | Cl | H | Cl | |
| 386 | 3-N(C$_3$H$_7$iso)CO$_2$C$_2$H$_5$ | Cl | H | Cl | |
| 387 | 3-N———O (ring) | Cl | H | Cl | |
| 388 | 3-N——— (ring) | Cl | H | Cl | |
| 389 | 3-NHCOOC$_4$H$_9$iso | Cl | H | Cl | |
| 390 | 3-NHCONHC$_4$H$_9$n | Cl | H | Cl | |
| 391 | 3-N———NH (ring) | Br | H | Br | |
| 392 | 3-N(CH$_3$)CON(CH$_3$)$_2$ | Cl | H | Cl | |
| 393 | 3-COOH | Cl | H | Cl | m.p. 250° C. |
| 394 | 3-COOCH$_3$ | Cl | H | Cl | m.p. 190–191° |
| 395 | 3-COOCH$_2$CH=CH$_2$ | Cl | H | Cl | m.p. 120–121° |
| 396 | 3-COOC$_3$H$_7$i | Cl | H | Cl | |
| 397 | 3-COCH$_2$—C≡C—C$_3$H$_7$n | Cl | H | Cl | |
| 398 | 3-CONH$_2$ | Cl | H | Cl | |
| 399 | 3-CONHOH | Cl | H | Cl | |
| 400 | 3-CON(CH$_3$)$_2$ | Cl | H | Cl | |
| 401 | 3-CONHCH$_3$ | Br | H | Br | |
| 402 | 3-CONHCH$_2$CH=CH$_2$ | Cl | H | F | |
| 403 | 3-COOC$_3$H$_6$N(CH$_3$)$_2$ | Cl | H | Cl | |
| 404 | 3-CHO | Cl | H | Cl | |
| 405 | 3-COCH$_3$ | Cl | H | Cl | |
| 406 | 3-CO—△ (cyclopropyl) | Cl | H | Cl | |
| 407 | 3-CSNHC$_4$H$_9$n | Cl | H | Cl | |
| 408 | 3-CSNHC$_3$H$_7$iso | Cl | H | Cl | |
| 409 | 3-CSN——— (ring) | Cl | H | Cl | |
| 410 | 3-N=CHC$_3$H$_7$(i) | Cl | H | Cl | |
| 411 | 3-N=C(CH$_3$)CH$_2$OCH$_3$ | Cl | H | Cl | |
| 412 | 3-N=CHC$_2$H$_4$OC$_2$H$_5$ | Cl | H | Cl | |

-continued

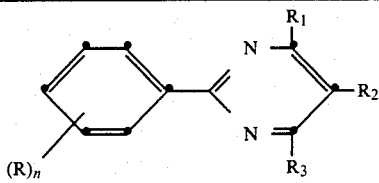

| No. | (R)$_n$ | R$_1$ | R$_2$ | R$_3$ | Physical data (°C.) |
|---|---|---|---|---|---|
| 413 | 3-N=C (ring) | Cl | H | Cl | |
| 414 | 3-SO$_2$NH$_2$ | Cl | H | Cl | m.p. 207–208° |
| 415 | 3-SO$_2$NHCH$_3$ | Cl | H | Cl | m.p. 174–175° |
| 416 | 3-SO$_2$N(C$_4$H$_9$n)$_2$ | Cl | H | Cl | |
| 417 | 3-SO$_2$N(morpholino) | Cl | H | Cl | |
| 418 | 3-SO$_2$N(CH$_3$)$_2$ | Cl | H | Cl | m.p. 144–145° |
| 419 | 3-CH(OC$_2$H$_5$)$_2$ | Cl | H | Cl | |
| 420 | 3-C(CH$_3$)(OCH$_3$)$_2$ | Cl | H | Cl | |
| 421 | 3-C(CH$_3$)(OC$_2$H$_4$OCH$_3$)$_2$ | Cl | H | Cl | |
| 422 | 3-CH—O (dioxolane) | Cl | H | Cl | |
| 423 | 3-C(CH$_3$)—O (dioxolane) | Cl | H | Cl | |
| 424 | 3-PO(OC$_2$H$_5$)$_2$ | Cl | H | Cl | |
| 425 | 3-P(OH)$_2$ | Cl | H | Cl | |
| 426 | 3-P(OH)OCH$_3$ | Cl | H | Cl | |
| 427 | 3-SO$_3$H | Cl | H | Cl | m.p. 95–96° |
| 428 | 3-CF$_3$ | Cl | H | F | |
| 429 | 3-CH$_2$CN | Cl | H | Cl | |
| 430 | 3-CH$_2$Cl | Cl | H | Cl | |
| 431 | 3-CH$_2$OC$_2$H$_5$ | Cl | H | Cl | |
| 432 | 3-CH$_2$OH | Br | H | Br | |
| 433 | 3-C$_2$H$_4$SCH$_3$ | Cl | H | Cl | |
| 434 | 3-C$_2$H$_4$SOCH$_3$ | Cl | H | Cl | |
| 435 | 3-CHCl—C$_2$H$_5$ | Cl | H | F | |
| 436 | 3-C$_3$H$_7$n | Cl | H | Cl | |
| 437 | 3-C$_6$H$_{13}$iso | Cl | H | Cl | |
| 438 | 3-C≡CH | Cl | H | Cl | |
| 439 | 3-C≡CCH$_3$ | Cl | H | Cl | |
| 440 | 3-CH=CH$_2$ | Cl | H | Cl | |
| 441 | 3-CCl=CH$_2$ | Cl | H | Cl | |
| 442 | 3-CCl=CHCH$_3$ | Cl | H | Cl | |
| 443 | 3-C$_2$H$_4$N(CH$_3$)$_2$ | Cl | H | Cl | |
| 444 | 3-cyclopropyl | Cl | H | Cl | |
| 445 | 3-CH=CH—C$_3$H$_7$n | Cl | H | Cl | |
| 446 | 3-(cyclopentadienyl) | Cl | H | Cl | |
| 447 | 3-CH$_2$COOC$_2$H$_5$ | Cl | H | Cl | |
| 448 | 3-CH$_2$CONH$_2$ | Br | H | Br | |
| 449 | 2-CH$_3$ | Br | H | Br | |
| 450 | 2-F | Cl | H | Cl | |
| 451 | 2-OCH$_2$C≡CH | Cl | H | Cl | |
| 452 | 2-SCH$_3$ | Cl | H | Cl | |
| 453 | 2-SH | Cl | H | Cl | |
| 454 | 2-COOH | Cl | H | Cl | |
| 455 | 2-COOCH$_3$ | Cl | H | Cl | |
| 456 | 2-CH$_2$OH | Br | H | Br | |
| 457 | 2-CHO | Cl | H | Cl | |
| 458 | 3-Cl, 4F | F | H | F | m.p. 101–103° |

-continued

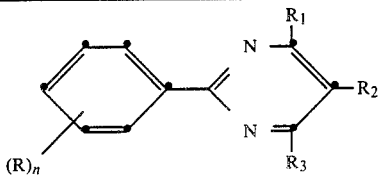

| No. | (R)n | R1 | R2 | R3 | Physical data (°C.) |
|---|---|---|---|---|---|
| 459 | 3-Cl, 4F | F | H | Cl | |
| 460 | 3,4(CH3)2 | Cl | H | Cl | |
| 461 | 3,5(Cl)2 | Cl | H | Cl | m.p. 175–177° |
| 462 | 2,6(Cl)2 | Cl | H | Cl | |
| 463 | 2,3(CH3)2 | Cl | H | Cl | |
| 464 | 2,4(CH3)2 | Cl | H | Cl | |
| 465 | 3-Cl, 4-C3H7iso | Cl | H | Cl | |
| 466 | 2-Cl, 4-CH3 | Cl | H | Cl | |
| 467 | 3,4(Cl)2 | Cl | H | Cl | |
| 468 | 3,5(OCH3)2 | Cl | H | Cl | m.p. 168–172° |
| 469 | 3-NH2, 4-CH3 | Cl | H | Cl | |
| 470 | 3-NHCH3, 4-CH3 | Cl | H | Cl | |
| 471 | 3-OH, 5-Cl | Cl | H | Cl | |
| 472 | 3-OCHF2, 5-Cl | Cl | H | Cl | |
| 473 | 3-OCH3, 5-Cl | Cl | H | Cl | |
| 474 | 3-COOH, 5-Cl | Cl | H | Cl | |
| 475 | 3-COOCH3, 5-Cl | Cl | H | Cl | |
| 476 | 3-CONH2, 5-Cl | Cl | H | Cl | |
| 477 | 4-COCH3, 4-CH3 | Cl | H | Cl | |
| 478 | 2-Cl, 6-C≡CH | Br | H | Br | |
| 479 | 4-SO2N(CH3)2, 5-CH3 | Br | H | Br | |
| 480 | 3-C≡CH, 5CH3 | Cl | H | F | |
| 481 | 2-CH3, 5-N(CH3)2 | Cl | H | Cl | |
| 482 | 2-CH3, 5-Cl | Cl | H | Cl | |
| 483 | 3-Br, 4-OCH3 | Cl | H | Cl | |
| 484 | 3-CH3, 4-NHCON(CH3)2 | Cl | H | Cl | |
| 485 | 2 SCH3, 5-NO2 | Cl | H | Cl | |
| 486 | 2 SCH3, 5-NH2 | Cl | H | Cl | |
| 487 | 2 Cl, 5-NO2 | Cl | H | Cl | |
| 488 | 2 Cl, 5NH2 | Cl | H | Cl | |
| 489 | 3,4(OCH3)2 | Cl | H | Cl | |
| 490 | 3,4 (OH)2 | Cl | H | Cl | m.p. 116–118° |
| 491 | 2,3.Cl2 | Cl | H | Cl | m.p. 127–129° |
| 492 | 2,5 (OCH3)2 | Cl | H | Cl | |
| 493 | 2,5 (OH)2 | Cl | H | Br | |
| 494 | 4-CN3, 3-CH3 | Cl | H | Cl | m.p. 120–123° |
| 495 | 4-OH, 3-CH3 | Cl | H | Br | |
| 496 | 4-OCH3, 3-NO2 | Cl | H | Cl | |
| 497 | 4-OH, 3-NO2 | Cl | H | Cl | |
| 498 | 4-OCH3, 3-NH2 | Cl | H | Cl | |
| 499 | 4-OH, 3-NH2 | Cl | H | Cl | |
| 500 | 3,5 (OH)2 | Cl | H | Cl | |
| 501 | 2,6 Cl2, 3-NO2 | Cl | H | Cl | |
| 502 | 2,6 Cl2, 3-NH2 | Cl | H | Cl | |
| 503 | 2,6(OCH3)2, 4-Cl | Br | H | Br | |
| 504 | 2,6(OH)2, 4-Cl | Br | H | Br | |
| 505 | 3,5(J)2, 4-OCH3 | Cl | H | Cl | |
| 506 | 3,5(J)2, 4-OH | Br | H | Br | |
| 507 | 3,5(Cl)2, 4-OCH3 | Br | H | Br | |
| 508 | 3,5(Cl)2, 4-OH | Cl | H | Cl | |
| 509 | 2,5(Cl2), 4-OCH3 | Cl | H | Cl | |
| 510 | 2,5(Cl)2, 4-OH | Cl | H | Cl | |
| 511 | 4F | Cl | H | Br | |
| 512 | 3,4(OH)2 | Br | H | Br | |
| 513 | 2,6(OH)2, 3-NH2 | Cl | H | Cl | |
| 514 | 3-OCH2OCH3 | Cl | H | Cl | |
| 515 | 3,5(OH)2, 4-OCH3 | Cl | H | Cl | |
| 516 | 3,4,5(OH)3 | Cl | H | Cl | |
| 517 | 2,3,4(OCH3)3 | Cl | H | Cl | |
| 518 | 2,3,4(OH)3 | Cl | H | Cl | |
| 519 | 2,3,5(Cl)3, 4-OCH3 | Cl | H | Cl | |
| 520 | (CH3)5 | Cl | H | Cl | |
| 521 | (H)5 | CN | H | CN | m.p. 150–155° |
| 522 | (H)5 | Cl | H | CN | |
| 523 | 4-CH3 | CN | H | CN | |
| 524 | 4-CH3 | Cl | H | CN | |
| 525 | 4-OCH3 | CN | H | CN | |
| 526 | 4-OCH | CN | H | Cl | |
| 527 | 4-OH | CN | H | CN | |
| 528 | 4-OH | Cl | H | CN | |
| 529 | (H)5 | SCH3 | H | Cl | |
| 530 | (H)5 | SO2CH3 | H | Cl | |

-continued

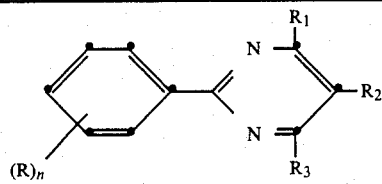

| No. | (R)$_n$ | R$_1$ | R$_2$ | R$_3$ | Physical data (°C.) |
|---|---|---|---|---|---|
| 531 | (H)$_5$ | SCH$_3$ | H | Br | |
| 532 | (H)$_5$ | SO$_2$CH$_3$ | H | Br | |
| 533 | (H)$_5$ | SCH$_3$ | H | F | |
| 534 | (H)$_5$ | SO$_2$CH$_3$ | H | F | |
| 535 | (H)$_5$ | CN | Cl | Cl | |
| 536 | 3-SCH$_2$CO$_2$CH$_3$ | Cl | H | Cl | |
| 537 | (H)$_5$ | OCF$_3$ | H | Cl | |
| 538 | 4-CH$_3$ | OCF$_3$ | H | Cl | |
| 539 | 4-CH$_3$ | OCOCH$_3$ | H | Cl | m.p. 110–112° |
| 540 | 4-OH, 3CH$_3$ | Cl | H | Cl | |
| 541 | (H)$_5$ | Cl | F | Cl | |
| 542 | (H)$_5$ | Br | F | Br | |
| 543 | 3-CH$_3$ | Cl | H | Cl | m.p. 76–79° |
| 544 | 3-SCH$_3$ | Cl | H | Cl | m.p. 103–105° |
| 545 | 3-CCl$_3$ | Cl | H | Cl | |
| 546 | 4-CCl$_3$ | Cl | H | Cl | |
| 547 | 4-OH, 3-CH$_3$ | Br | H | Cl | m.p. 140–145° |
| 548 | 4-SCH$_2$COCH$_3$ | Cl | H | Cl | |
| 549 | 3-SCOCH=CH$_2$ | Cl | H | Cl | |
| 550 | 4-SCOCH=CHCH$_3$ | Cl | H | Cl | |
| 551 | 3-SCO—CH$_2$C≡CH | Br | H | Br | |
| 552 | 4-SOCH$_2$CH=CH$_2$ | Cl | H | Cl | |
| 553 | 3-SOCH$_2$CH=CH$_2$ | Cl | H | Cl | |
| 554 | 4-SOCH$_2$C≡CH | F | H | Cl | |
| 555 | 3-SOCH$_2$C≡CH | Cl | H | Cl | |
| 556 | 3-SO$_2$CH$_2$CH=CH$_2$ | Br | H | Br | |
| 557 | 4-SO$_2$CH$_2$CH=CH$_2$ | Cl | H | Cl | |
| 558 | 3-SO$_2$CH$_2$C≡CH | Cl | H | Cl | |
| 559 | 4-SO$_2$CH$_2$C≡CH | Cl | H | Cl | |
| 560 | 4-OCOC$_6$H$_{13}$n | Cl | H | Cl | |
| 561 | 3-OCO—C$_5$H$_{11}$i | Cl | H | Cl | |
| 562 | 4-OCONHCH$_3$ | Cl | H | Cl | m.p. 205–209° |
| 563 | 3-OCONHCH$_3$ | Cl | H | Cl | m.p. 134–137° |
| 564 | 4-OCON(CH$_3$)$_2$ | Cl | H | Cl | m.p. 191–193° |
| 565 | 4-OCONHC$_4$H$_9$ | Cl | H | Cl | |
| 566 | 3-OCONHC$_3$H$_7$i | Cl | H | Cl | |
| 567 | 4-OCOCH=CH$_2$ | Cl | H | Cl | |
| 568 | 3-OCOCH=CH—CH$_3$ | Cl | H | Cl | |
| 569 | 4-OCOCH$_2$OCH$_3$ | Cl | H | Cl | |
| 570 | 3-OCON(CH$_3$)$_2$ | Cl | H | Cl | |
| 571 | 4-NHCONHC$_4$H$_9$n | Cl | H | Cl | |
| 572 | 4-SH | Cl | H | Cl | |
| 573 | 3-OC$_2$H$_4$OH | Cl | H | Cl | |
| 574 | 3-NHC$_2$H$_4$COOCH$_3$ | Cl | H | Cl | |
| 575 | 3-Br, 4-OH | Cl | H | Cl | |
| 576 | 3-NHCONHCH$_3$ | Cl | H | Cl | m.p. 234–238° |
| 577 | 4-OCH$_3$ | OH | H | OH | m.p. 318° Z |

FORMULATION EXAMPLES

The compounds of formula I will normally not be used by themselves in agriculture. They are used in the form of ready-for-use formulations which can be applied either direct or diluted with water.

EXAMPLE 8

Dusts: The following substances are used to formulate (a) a 5% and (b) a 2% dust:

| (a) | 5 parts of 2-p-tolyl-4,6-bis-isopropoxypyrimidine or of a mixture thereof with 2-chloro-2',6'-diethyl-N—(butoxymethyl)-acetanilide |
| | 95 parts of talcum; |
| (b) | 2 parts of the above active ingredient or a mixture |
| | 1 part of highly dispersed silicic acid |

-continued 97 parts of talc;

The active ingredients are mixed with the carriers and ground and in this form can be processed to dusts for application.

EXAMPLE 9

Granulate: The following substances are used to formulate a 5% granulate:

| | 5 parts of 2-p-tolyl-4,6-isopropoxy-5-bromopyrimidine or of a mixture thereof with 2-chloro-2',6'-diethyl-N—(methoxymethyl)-acetanilide |
| | 0.25 part of epoxidised vegetable oil |
| | 0.25 part of cetyl polyglycol ether |
| | 3.25 parts of polyethylene glycol |

-continued 91 parts of kaolin (particle size 0.3–0.8 mm).

The active ingredient or mixture is mixed with the vegetable oil and the mixture is dissolved in 6 parts of acetone. Then polyethylene glycol and cetyl polyglycol ether are added. The resultant solution is sprayed on kaolin and the acetone is evaporated in vacuo. A microgranular formulation of this kind can be conveniently incorporated in seed furrows.

EXAMPLE 10

Wettable powders: The following constituents are used to formulate (a) a 70%, (b) a 40%, (c) and (d) a 25% and (e) a 10% wettable powder:

| | | |
|---|---|---|
| (a) | 70 | parts of 2-p-tolyl-4,6-bis-(methoxyethyl)-5-chloro-pyrimidine or a mixture thereof with 2-chloro-2',6'-diethyl-N—(2''-propoxyethyl)-acetanilide |
| | 5 | parts of sodium dibutylnaphthylsulfonate |
| | 3 | parts of naphthalenesulfonic acid/phenolsulfonic acid/formaldehyde condensate (3:2:1) |
| | 10 | parts of kaolin |
| | 12 | parts of Champagne chalk |
| (b) | 40 | parts of active ingredient or mixture as above, |
| | 5 | parts of sodium lignosulfonate |
| | 1 | part of sodium dibutylnaphthalenesulfonate |
| | 54 | parts of silicic acid |
| (c) | 25 | parts of active ingredient or mixture as above |
| | 4.5 | parts of calcium lignosulfonate |
| | 1.9 | parts of Champagne chalk/hydroxyethyl cellulose mixture (1:1) |
| | 1.5 | parts of sodium dibutylnaphthalenesulfonate |
| | 19.5 | parts of silicic acid |
| | 19.5 | parts of Champagne chalk |
| | 28.1 | parts of kaolin |
| (d) | 25 | parts of active ingredient or mixture as above |
| | 2.5 | parts of isooctylphenoxy polyethylene ethanol |
| | 1.7 | parts of a Champagne chalk/hydroxyethyl cellulose mixture (1:1) |
| | 8.3 | parts of sodium aluminium silicate |
| | 16.5 | parts of kieselguhr |
| | 46 | parts of kaolin |
| (e) | 10 | parts of active ingredient or mixture as above |
| | 3 | parts of a mixture of the sodium salts of saturated fatty alcohol sulfates |
| | 5 | parts of naphthalenesulfonic acid/formaldehyde condensate |
| | 82 | parts of kaolin. |

The active ingredients are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for leaf application (to inhibit growth or for fungicidal application).

EXAMPLE 11

Emulsifiable concentrate: The following substances are used to formulate a 25% emulsifiable concentrate:

| | |
|---|---|
| 25 | parts of 2-phenyl-4-chloro-6-methylpyrimidine or of a mixture thereof with 2-chloro-6'-ethyl-N—(2''-methoxy-1''-methylethyl)-acet-o-toluidide |
| 2.5 | parts of epoxidised vegetable oil |
| 10 | parts of an alkylarylsulfonate/fatty alcohol polyglycol ether mixture |
| 5 | parts of dimethyl formamide |
| 57.5 | parts of xylene. |

EXAMPLE 12

Paste: The following substances are used to formulate a 45% paste:

| | | |
|---|---|---|
| (a) | 45 | parts of 2-phenyl-4-chloro-6-hydroxypyrimidine or of a mixture thereof with 2-chloro-2',6'-diethyl-N—(methoxymethyl)-acetanilide |
| | 5 | parts of sodium aluminium silicate, |
| | 14 | parts of cetyl polyglycol ether with 8 moles of ethylene oxide, |
| | 3 | parts of oleyl polyglycol ether with 5 moles of ethylene oxide, |
| | 2 | parts of spindle oil, |
| | 10 | parts of polyethylene glycol, |
| | 23 | parts of water. |
| (b) | 45 | parts of the above active ingredient or mixture |
| | 5 | parts of ethylene glycol, |
| | 3 | parts of octylphenoxy polyethylene glycol containing 9–10 moles of ethylene oxide per mole of octylphenol, |
| | 3 | parts of a mixture of aromatic sulfonesulfonic acids, condensed with formaldehyde as ammonium salt, |
| | 1 | part of silicone oil in form of a 75% emulsion, |
| | 0.1 | part of a mixture of 1-(3-chloroallyl)-3,5,7-triazo-azonium-adamantane chloride with sodium carbonate (chloride value at least 11.5%), |
| | 0.2 | part of a biopolymeric thickener containing a maximum of 100 bacilli per gram, |
| | 42.7 | parts of water. |

The active ingredient is intimately mixed with the adjuvants in appropriate devices and ground. By diluting the resultant paste with water, it is possible to prepare suspensions of the desired concentration.

BIOLOGICAL EXAMPLES

The ability of the compounds of formula I to protect cultivated plants from the phytotoxic effects of potent herbicides can be seen from the following Examples. In the test procedures, the compounds of formula I are designated as antidotes. The protective action is indicated in percent. 0% denotes the action of the herbicide when applied by itself; 100% denotes the desired normal growth of the cultivated plant. A protective action of at least 10% is significant.

EXAMPLE 13

Tests with antidote and herbicide in transplanted rice. Method of application: tank mixture Rice plants are reared in soil to the 1½- to 2-leaf stage. The plants are then transplanted in bunches (always 3 plants together) in sandy loam in containers measuring 47 cm×29 cm×24 cm. The surface of the soil is then covered with water to a height of 1.5 to 2 cm. Two to three days after transplantation, the herbicide and the antidote as test substance are applied together direct to the water as tank mixture. The protective action of the antidote is evaluated in percent 24 days after transplantation. The plants treated with herbicide alone (no protective action) as well as the completely untreated controls (100% growth) serve as references for the evaluation. The results are reported below.

| Antidote compound | Rate of application in kg/ha | Herbicide rate of application in kg/ha | Protective action in % |
|---|---|---|---|
| Herbicide: 2-chloro-2',6'-diethyl-N—(2''-propoxyethyl)-acetanilide "Pretilachlor". | | | |
| 1 | 1 | 1 | 50 |

-continued

| Antidote compound | Rate of application in kg/ha | Herbicide rate of application in kg/ha | Protective action in % |
|---|---|---|---|
| 2 | 0.75 | 0.75 | 25 |
| 49 | 0.75 | 0.75 | 12.5 |
| 50 | 1 | 1 | 12.5 |
| 53 | 1.5 | 1.5 | 25 |
| 59 | 1 | 1 | 25 |
| 84 | 1 | 1 | 25 |
| 99 | 1 | 1 | 25 |
| Herbicide: 2-chloro-2',6'-diethyl-N—(butoxymethyl)acetanilide "Butachlor" | | | |
| 2 | 1.5 | 1.5 | 12.5 |
| 49 | 1.5 | 1.5 | 12.5 |
| 50 | 1.5 | 1.5 | 25 |
| 53 | 1.5 | 1.5 | 12.5 |
| 54 | 1.5 | 1.5 | 12.5 |
| Herbicide: 2-chloro-2',6'-diethyl-N—(methoxymethyl)acetanilide "Alachlor" | | | |
| 1 | 0.125 | 0.125 | 12 |
| 2 | 0.125 | 0.125 | 25 |
| 49 | 0.125 | 0.126 | 25 |
| Herbicide: 2-chloro-6'-ethyl-N—(ethoxymethyl)cet-o-toluidide "Acetochlor" | | | |
| 2 | 0.125 | 0.125 | 12.5 |
| 49 | 0.125 | 0.125 | 12.5 |
| Herbicide: 2,6-dinitro-N,N—dipropyl-4-trifluoromethylaniline "Trifluralin" | | | |
| 2 | 2 | 2 | 12.5 |
| Herbicide: S—4-chlorobenzyl-diethylthiocarbamate "Thiobencarb" | | | |
| 1 | 8 | 8 | 50 |
| 1 | 4 | 4 | 25 |
| 1 | 2 | 2 | 12.5 |

Rice is likewise protected from the phytotoxic effects of S-benzyl-N,N-diethylthiocarbamate.

EXAMPLE 14

Test with antidote and herbicide in transplanted rice

Method of application: root treatment

Rice plants of the Yamabiko variety are reared in soil to the 1½- to 2-leaf stage and then washed. The roots only of the plants in bunches (always 3 plants together) are then immersed for 15 to 60 minutes in a dish containing a solution of the compound to be tested as antidote in a concentration of 1000 ppm. The plants are then transplanted in sandy loam in containers measuring 47 cm×29 cm×24 cm. The surface of the soil is then covered with water to a height of 1.5 to 2 cm. Two to three days after transplantation, the herbicide is applied direct to the water. The protective action of the antidote is evaluated in percent 24 days after transplantation. The plants treated with the herbicide alone (no protective action) as well as the completely untreated controls (100% growth) serve as references for the evaluation. The results are as follows:

| Herbicide: 2-chloro-2',6'-diethyl-N—(2''-propoxyethyl)-acetanilide "Pretilachlor" | | | |
|---|---|---|---|
| Antidote compound | Rate of application | Herbicide rate of application in kg/ha | Protective action in % |
| 1 | 1000 ppm | 0.75 | 87.5 |
| 2 | 1000 ppm | 1 | 50 |

EXAMPLE 15

Test with antidote and herbicide in transplanted rice. Application of the antidote to the plant using an aqueous solution (drench method)

Rice plants of the Yamabiko variety are reared in seed dishes to the 1½ to 2-leaf stage. 1 to 2 days before transplantation, each seed dish with the rice plants is immersed in a larger dish containing a solution of the compound to be tested as antidote in a concentration of 1000 ppm. The plants are then transplanted in bunches (always 3 plants together) in sandy loam in containers measuring 47 cm×29 cm×24 cm. The surface of the soil is then covered with water to a height of 1.5 to 2 cm. Two to three days after transplantation, the herbicide is applied direct to the water. The protective action of the antidote is evaluated in percent 24 days after transplantation. The plants treated with the herbicide alone (no protective action) as well as the completely untreated controls (100% growth) serve as references for the evaluation. The result is as follows:

| Herbicide: 2-chloro-2',6'-diethyl-N—(2''-propoxyethyl)-acetanilide "Pretilachlor" | | | |
|---|---|---|---|
| Antidote compound | Rate of application | Herbicide rate of application in kg/ha | Protective action in % |
| 2 | 1000 ppm | 1 | 37.5 |

EXAMPLE 16

Test with antidote and herbicide in transplanted rice. Preemergence application of the antidote The compound to be tested as antidote is sprayed in the form of a dilute solution to the most surface of soil in seed dishes. Rice seeds are then sown in the dishes and reared to to the 1½- to 2-leaf stage. The plants are then transplanted in bunches (always 3 plants together) in sandy loam in containers measuring 47 cm×29 cm×24 cm. The surface of the soil is then covered with water to a height of 1.5 to 2 cm. Two to three days after transplantation, the herbicide is applied direct to the water. The protective action of the antidote is evaluated in percent 24 days after transplantation. The plants treated with the herbicide alone (no protective action) as well as the completely untreated controls (100% growth) serve as references for the evaluation. The result is as follows:

| Herbicide: 2-chloro-2',6'-diethyl-N—(2''-propyloxyethyl)-acetanilide "Pretilachlor" | | | |
|---|---|---|---|
| Antidote compound | Rate of application | Herbicide rate of application in kg/ha | Protective action in % |
| 2 | 4 | 1.5 | 25 |

EXAMPLE 17

Test with antidote and herbicide in transplanted rice. Pre-plant incorporation method The compound to be tested as antidote is incorporated in the soil in seed dishes in a concentration of 100 ppm. Two days later the rice plants are reared in the treated seed dishes to the 1½- to 2-leaf stage. The plants are then transplanted in bunches (always 3 plants together) in sandy loam in containers measuring 47 cm×29 cm×24 cm. The surface of the soil is then covered with water to a height of 1.5 to 2 cm. Two to three days after transplantation, the herbicide is applied direct to the water. The protective action of the antidote is evaluated in percent 24 days after transplantation. The plants treated with the herbicide alone (no protective action) as well as the completely untreated controls (100% growth) serve as references for the evaluation. The results are as follows:

| Herbicide: 2-chloro-2',6'-diethyl-N—(2"-propoxyethyl)-acetanilide "Pretilachlor" | | | |
|---|---|---|---|
| Antidote compound | Rate of application | Herbicide rate of application in kg/ha | Protective action in % |
| 2 | 100 ppm | 1 | 25 |
| 2 | 100 ppm | 0.75 | 25 |

EXAMPLE 18

Test with antidote and herbicide in transplanted rice. Postemergence application of the antidote (over the top application)

Rice plants of the Yamabiko variety are reared in soil to the 1½- to 2-leaf stage. The compound to be tested as antidote is then sprayed in the form of a dilute solution over the rice plants. Two days later the plants are then transplanted in bunches (always 2 plants together) in sandy loam in containers measuring 47 cm×29 cm×24 cm. The surface of the soil is then covered with water to a height of 1.5 to 2 cm. Two to three days after transplantation, the herbicide is applied direct to the water. The protective action of the antidote is evaluated in percent 24 days after transplantation. The plants treated with the herbicide alone (no protective action) as well as the completely untreated controls (100% growth) serve as references for the evaluation. The result is as follows:

| Herbicide: 2-chloro-2',6'-diethyl-N—(2"-propoxyethyl)-acetanilide "Pretilachlor" | | | |
|---|---|---|---|
| Antidote compound | Rate of application in kg/ha | Herbicide rate of application in kg/ha | Protective action in % |
| 2 | 4 | 1.5 | 12 |

The 2-phenylpyrimidines of this invention employed in the test methods described in Examples 13 to 18 also exerted a certain protective action on the transplanted rice when the following herbicides were used instead of those indicated above: S-2-methylpiperidino-carbonylmethyl-O,O-dipropylphosphorodithioate ("Piperophos"), S-ethyl-N,N-hexamethylenethiocarbamate ("Molinate"), S-4-chlorobenzyl-diethyl-thiocarbamate ("Thiobencarb"), S-4-benzyl-diethyl-thiocarbamate, 5-tert-butyl-3-(2,4-dichloro-5-isopropoxyphenyl)-1,3,4-oxadiazol-2-one ("Oxadiazon") or N-(3,4-dichlorophenyl)-propionamide ("Propanil").

EXAMPLE 19

Test with antidote and herbicide with rice sown in water. (The rice seeds are soaked and sown direct in very wet, marshy or flooded soil. Application of the antidote as tank mixture)

Rice seeds are soaked for 48 hours in water. Plastic containers measuring 25 cm×17 cm×12 cm are filled with soil into which the soaked seeds are sown. The compound to be tested as antidote and the herbicide are then sprayed together as tank mixture onto the surface of the soil. The water level is raised gradually in accordance with the growth of the rice plants. The protective action of the antidote is evaluated in percent 21 days later. The plants treated with herbicide alone (no protective action) as well as the completely untreated controls (100% growth) serve as references for the evaluation. The results are reported in the following table.

| Antidote compound | Rate of application in kg/ha | Herbicide rate of application in kg/ha | Protective action in % |
|---|---|---|---|
| Herbicide: 2-chloro-2',6'-diethyl-N—(2"-propoxyethyl)-acetanilide "Pretilachlor" | | | |
| 1 | 0.25 | 0.25 | 62.5 |
| 2 | 0.25 | 0.25 | 50 |
| 49 | 0.25 | 0.25 | 37.5 |
| 50 | 0.25 | 0.25 | 50 |
| 53 | 0.25 | 0.25 | 62.5 |
| 54 | 0.25 | 0.25 | 62.5 |
| 57 | 0.25 | 0.25 | 50 |
| 59 | 0.25 | 0.25 | 75 |
| 64 | 0.25 | 0.25 | 12.5 |
| 67 | 0.25 | 0.25 | 37.5 |
| 84 | 0.25 | 0.25 | 75 |
| 89 | 0.25 | 0.25 | 25 |
| 99 | 0.25 | 0.25 | 62.5 |
| 129 | 0.25 | 0.25 | 37.5 |
| 130 | 0.25 | 0.25 | 62.5 |
| 132 | 0.25 | 0.25 | 37.5 |
| 134 | 0.25 | 0.25 | 62.5 |
| 135 | 0.25 | 0.25 | 50 |
| 158 | 0.25 | 0.25 | 50 |
| 197 | 0.25 | 0.25 | 25 |
| 198 | 0.25 | 0.25 | 62.5 |
| 200 | 0.25 | 0.25 | 50 |
| 209 | 0.25 | 0.25 | 25 |
| 223 | 0.25 | 0.25 | 62.5 |
| 248 | 0.25 | 0.25 | 62.5 |
| 347 | 0.25 | 0.25 | 62.5 |
| 381 | 0.25 | 0.25 | 25 |
| 394 | 0.25 | 0.25 | 25 |
| 461 | 0.25 | 0.25 | 37.5 |
| 468 | 0.25 | 0.25 | 25 |
| 491 | 0.25 | 0.25 | 75 |
| Herbicide: 2-chloro-2',6'-diethyl-N—(butoxymethyl)-acetanilide "Butachlor" | | | |
| 1 | 0.5 | 0.15 | 37.5 |
| 2 | 0.75 | 0.75 | 50 |
| 49 | 0.75 | 0.75 | 50 |
| 50 | 0.75 | 0.75 | 37.5 |
| 53 | 0.75 | 0.75 | 62.5 |
| 54 | 0.75 | 0.75 | 62.5 |
| Herbicide: 2-chloro-2',6'-diethyl-N—(methoxymethyl)-acetanilide "Alachlor" | | | |
| 1 | 0.03 | 0.03 | 25 |
| 2 | 0.03 | 0.03 | 12.5 |
| 49 | 0.03 | 0.03 | 37.5 |
| 50 | 0.03 | 0.03 | 37.5 |
| 53 | 0.03 | 0.03 | 25 |
| 54 | 0.03 | 0.03 | 37.5 |
| Herbicide: 2-chloro-6'-ethyl-N—(2"-methoxy-1"-methylethyl)-acet-o-toluidide, "Metolachlor" | | | |
| 1 | 0.03 | 0.03 | 25 |
| 2 | 0.03 | 0.03 | 12.5 |
| 49 | 0.03 | 0.03 | 25 |
| 50 | 0.03 | 0.03 | 12.5 |
| 53 | 0.03 | 0.03 | 25 |
| 54 | 0.03 | 0.03 | 12.5 |
| Herbicide: S—ethyl-diisopropylthiocarbamate, "EPTC" | | | |
| 1 | 1 | 1 | 25 |
| Herbicide: S—2-methylpiperidino-carbonylmethyl-O,O—dipropylphosphothioate, "Piperophos" | | | |
| 1 | 0.5 | 0.5 | 37.5 |
| Herbicide: 5-ethyl-N,N—hexamethylene-thiocarbamate | | | |

-continued

| Antidote compound | Rate of application in kg/ha | Herbicide rate of application in kg/ha | Protective action in % |
|---|---|---|---|
| "Molinate" | | | |
| 1 | 2 | 2 | 25 |
| Herbicide: S—4-chlorobenzyl-diethylthiocarbamate "Thiobencarb" | | | |
| 1 | 4 | 4 | 37.5 |

The antidote, compound 1, as well as other 2-phenyl-pyrimidines of this invention, were also able to protect rice from the phytotoxic effects of S-4-benzyl-diethyl-thiocarbamate and 5-tert-butyl-3-(2,4-dichloro-5-iso-propoxyphenyl)-1,3,4-oxdiazol-2-one ("Oxdiazon").

EXAMPLE 20

Test with antidote and herbicide with rice sown in water. Application of the antidote while soaking the rice seeds Rice seeds are soaked for 48 hours in solutions of the test antidote at a concentration of 100 ppm. The seeds are then allowed to dry for about 2 hours until they are no longer tacky. Plastic containers measuring 25 cm × 17 cm × 12 cm are filled with sandy loam to 2 cm below the edge. The soaked seeds are sown on the surface of the soil in the containers and then very lightly covered. The soil is kept in a moist (non-marshy) state. Then a dilute solution of the herbicide is sprayed onto the surface of the soil. The water level is raised gradually in accordance with the growth of the plants. Evaluation of the protective action in percent is made 21 days later. The plants treated with herbicide alone (no protective action) as well as the completely untreated controls (100% growth) serve as references for the evaluation. The results are reported in the following table.

| Antidote compound | Rate of application | Herbicide rate of application in kg/ha | Protective action in % |
|---|---|---|---|
| Herbicide: 2-chloro-2',6'-diethyl-N—(2'''-propoxyethyl)-acetanilide "Pretilachlor". | | | |
| 1 | 100 ppm | 0.25 | 62.5 |
| 2 | 100 ppm | 0.25 | 75 |
| 49 | 100 ppm | 0.25 | 75 |
| 50 | 100 ppm | 0.25 | 87.5 |
| 53 | 100 ppm | 0.25 | 62.5 |
| 54 | 100 ppm | 0.25 | 62.5 |
| 57 | 100 ppm | 0.25 | 50 |
| 59 | 100 ppm | 0.25 | 62.5 |
| 64 | 100 ppm | 0.25 | 50 |
| 67 | 100 ppm | 0.25 | 50 |
| 84 | 100 ppm | 0.25 | 50 |
| 89 | 100 ppm | 0.25 | 62.5 |
| 99 | 100 ppm | 0.25 | 62.5 |
| 128 | 100 ppm | 0.25 | 50 |
| 130 | 100 ppm | 0.25 | 50 |
| 132 | 100 ppm | 0.25 | 37.5 |
| 134 | 100 ppm | 0.25 | 50 |
| 135 | 100 ppm | 0.25 | 50 |
| 158 | 100 ppm | 0.25 | 75 |
| 197 | 100 ppm | 0.25 | 62.5 |
| 198 | 100 ppm | 0.25 | 75 |
| 200 | 100 ppm | 0.25 | 75 |
| 209 | 100 ppm | 0.25 | 62.5 |
| 223 | 100 ppm | 0.25 | 25 |
| 248 | 100 ppm | 0.25 | 50 |
| 347 | 100 ppm | 0.25 | 50 |
| 381 | 100 ppm | 0.25 | 62.5 |
| 394 | 100 ppm | 0.25 | 50 |
| 461 | 100 ppm | 0.25 | 62.5 |
| 468 | 100 ppm | 0.25 | 75 |
| 491 | 100 ppm | 0.25 | 37.5 |
| Herbicide: 2-chloro-2',6'-diethyl-N—(butoxymethyl)-acetanilide "Butchlor" | | | |
| 1 | 100 ppm | 0.5 | 50 |
| 2 | 100 ppm | 0.5 | 50 |
| 49 | 100 ppm | 0.5 | 37.5 |
| 50 | 100 ppm | 0.5 | 50 |
| 53 | 100 ppm | 0.5 | 50 |
| 54 | 100 ppm | 0.5 | 50 |
| Herbicide: 2-chloro-2',6'-diethyl-N—(methoxyethyl)-acetanilide "Alachlor" | | | |
| 1 | 100 ppm | 0.03 | 50 |
| 2 | 100 ppm | 0.03 | 62.5 |
| 49 | 100 ppm | 0.03 | 50 |
| 50 | 100 ppm | 0.03 | 62.5 |
| 53 | 100 ppm | 0.03 | 62.5 |
| 54 | 100 ppm | 0.03 | 50 |
| Herbicide: 2-chloro-6'-ethyl-N—(2''-methoxy-1''-methylethyl)-acet-o-toluidide, "Metolachlor" | | | |
| 2 | 100 ppm | 0.03 | 12.5 |
| 49 | 100 ppm | 0.03 | 12.5 |
| Herbicide: S—ethyl-diisopropylthiocarbamate, "EPTC" | | | |
| 1 | 100 ppm | 0.5 | 12.5 |
| Herbicide: S—2-methylpiperidino-carbonylmethyl-O,O—dipropyl-phosphorodithioate, "Piperophos" | | | |
| 1 | 1000 ppm | 6.5 | 37.5 |
| 1 | 100 ppm | 6.5 | 37.5 |
| 1 | 10 ppm | 6.5 | 25 |
| Herbicide: S—ethyl-N,N—hexamethylenethiocarbamate "Molinate" | | | |
| 1 | 1000 ppm | 8 | 62.5 |
| 1 | 100 ppm | 8 | 62.5 |
| 1 | 10 ppm | 8 | 62.5 |
| 1 | 1000 ppm | 2 | 37.5 |
| 1 | 100 ppm | 2 | 37.5 |
| 1 | 10 ppm | 2 | 37.5 |
| Herbicide: S—4-chlorobenzyl-diethylthiocarbamate "Thiocarb" | | | |
| 1 | 1000 ppm | 8 | 37.5 |
| 1 | 100 ppm | 8 | 37.5 |
| 1 | 1000 ppm | 4 | 50 |
| 1 | 100 ppm | 4 | 50 |
| 1 | 10 ppm | 4 | 37.5 |
| 1 | 1000 ppm | 2 | 37.5 |
| 1 | 100 ppm | 2 | 25 |
| 1 | 10 ppm | 2 | 25 |

Rice was also protected from the phytotoxic effects of S-benzyldiethylthiocarbamate and 5-tert-butyl-3-(2,4-dichloro-5-isopropoxyphenyl)-1,3,4-oxdiazol-2-one ("Oxdiazon").

EXAMPLE 21

Test with antidote and herbicide with rice sown in water. Application of antidote and herbicide in nutrient solution Seeds which would normally be damaged in the test concentrations of the herbicide employed are sown in granular zonolith (expanded vermiculite) in plastic flower pots (diameter 6 cm at the top) which are perforated at the bottom. Each pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid in daily replenished to 50 ml with a Hewitt nutrient solution. Evaluation of the protective action in percent is made 3 weeks fter the start of the test. The plants treated with herbicide alone (no protective action) as well as the completely untreated controls (100% growth) serve as references for the evaluation. The results are as follows:

| Herbicide: 2-chloro-2',6'-diethyl-N—(2''-propyloxyethyl)-acetanilide, "Pretilachlor" | | | |
|---|---|---|---|
| Antidote compound | Rate of application | Herbicide rate of application | Protective action in % |
| 1 | 10 ppm | 4 ppm | 75 |

EXAMPLE 22

Test with antidote and herbicide with rice sown dry (20 days after sowing, when the rice plants have attained the 3-leaf stage, the soil is flooded). Application of antidote and herbicide as tank mixture Rice seeds of the IR-36 variety are sown in containers measuring 47 cm×29 cm×24 cm, covered and gently pressed firm. The test antidote and the herbicide are then sprayed together as tank mixture onto the soil. About 20 days after sowing, when the rice plants have attained the 3-leaf stage, the surface of the soil is covered with water to a height of 4 cm. The protective action of the antidote is evaluated in percent 30 days after transplantation. The plants treated with herbicide alone (no protective action) as well as the completely untreated controls (100% growth) serve as references for the evaluation. The results are reported in the following table.

| Antidote compound | Rate of application in kg/ha | Herbicide rate of application in kg/ha | Protective action in % |
|---|---|---|---|
| Herbicide: 2-chloro-2,'6'-diethyl-N—(2''-propyloxyethyl)-acetanilide, "Pretilachlor" | | | |
| 1 | 2 | 2 | 62.5 |
| 2 | 2 | 2 | 50 |
| 49 | 2 | 2 | 50 |
| 50 | 2 | 2 | 50 |
| 53 | 2 | 2 | 62.5 |
| 54 | 2 | 2 | 50 |
| 59 | 2 | 2 | 50 |
| 84 | 3 | 3 | 62.5 |
| 99 | 2 | 2 | 27.5 |
| Herbicide: 2-chloro-2',6'-diethyl-N—(butoxymethyl)-acetanilide, "Butachlor" | | | |
| 1 | 3 | 3 | 25 |
| 2 | 3 | 3 | 25 |
| 49 | 3 | 3 | 37.5 |
| 50 | 3 | 3 | 37.5 |
| 53 | 3 | 3 | 25 |
| 54 | 3 | 3 | 37.5 |
| Herbicide: 2-chloro-2,6-diethyl-N—(methoxymethyl)-acetanilide "Alachlor" | | | |
| 1 | 0.25 | 0.25 | 37.5 |
| 2 | 0.5 | 0.5 | 25 |
| 49 | 0.5 | 0.5 | 12.5 |
| 50 | 0.25 | 0.25 | 25 |
| 53 | 0.25 | 0.25 | 25 |
| 54 | 0.5 | 0.5 | 25 |
| Herbicide: 2-chloro-6-ethyl-N—(2''-methoxy-1''-methylethyl)-acet-o-toluidide, "Metolachlor" | | | |
| 1 | 3 | 0.75 | 37.5 |
| Herbicide: 2-chloro-6-ethyl-N—(ethoxymethyl)-acet-o-toluidide "Acetochlor" | | | |
| 1 | 0.25 | 0.25 | 25 |
| 2 | 0.25 | 0.25 | 12.5 |
| 49 | 0.25 | 0.25 | 12.5 |
| 50 | 0.25 | 0.25 | 12.5 |
| 53 | 0.25 | 0.25 | 12.5 |
| 54 | 0.25 | 0.25 | 12.5 |
| Herbicide: 2,6-dinitro-N,N—dipropyl-4-trifluoromethylaniline "Trifluralin" | | | |
| 1 | 1 | 1 | 37.5 |
| 2 | 1 | 1 | 25 |
| 50 | 1 | 1 | 12.5 |
| 53 | 1 | 1 | 25 |
| 54 | 1 | 1 | 37.5 |
| Herbicide: 2,6-dichlorobenzonitrile, "Dichlobenil" | | | |
| 1 | 0.5 | 0.5 | 12.5 |
| 2 | 0.5 | 0.5 | 12.5 |
| 49 | 0.5 | 0.5 | 25 |
| 50 | 0.5 | 0.5 | 25 |
| 53 | 0.5 | 0.5 | 25 |
| 54 | 0.5 | 0.5 | 25 |
| Herbicide: S—2,3,3-trichloroallyl-diisopropylthiocarbamate "Tri-allate" | | | |
| 1 | 4 | 4 | 12.5 |
| 2 | 4 | 4 | 25 |
| 49 | 4 | 4 | 12.5 |
| 50 | 4 | 4 | 25 |
| 53 | 4 | 4 | 25 |
| 54 | 4 | 4 | 25 |

EXAMPLE 23

Test with antidote and herbicide in rice sown dry. Application of the antidote as seed dressing Rice seeds are mixed with the test antidote in a glass container. Seeds and test compound are well mixed by shaking and rotating. Containers measuring 47 cm×29 cm×24 cm are then filled with sandy loam and the dressed seeds are sown therein. The seeds are covered and a dilute solution of the herbicide is then sprayed onto the surface of the soil. About 20 days after sowing, when the rice plants have attained the 3-leak stage, the surface of the soil is covered with water to a height of 4 cm. The protective action of the antidote is evaluated in percent 30 days after application of the herbicide. The plants treated with herbicide alone (no protective action) as well as the completely untreated controls (100% growth) serve as references for the evaluation. The results are as follows:

| Antidote compound | Rate of application in g per kg of seeds | Herbicide rate of application in kg/ha | Protective action in % |
|---|---|---|---|
| Herbicide: 2-chloro-2',6'-diethyl-N—(2''-propyloxyethyl)-acetanilide, "Pretilachlor" | | | |
| 1 | 2 g | 3 | 37.5 |
| Herbicide: 2-chloro-6'-ethyl-N—(2''-methoxy-1''-methylethyl)-acet-o-toluidide, "Metolachlor" | | | |
| 1 | 1 g | 0.5 | 62.5 |

EXAMPLE 24

Test with antidote and herbicide in dry rice (the rice is sown dry and watered by natural rainfall). Application of antidote and herbicide as tank mixture Rice seeds are sown in containers measuring 47 cm×29 cm×24 cm, covered, and gently pressed firm. A dilute solution of the test antidote together with the herbicide is then sprayed as tank mixture onto the soil. Evaluation of the protective action of the antidote is made in percent 24 days after sowing. The plants treated with herbicide alone (no protective action) as well as the completely untreated controls (100% growth) serve as references for the evaluation. The results are reported in the following table.

| Antidote compound | Rate of application in kg/ha | Herbicide rate of application in kg/ha | Protective action in % |
|---|---|---|---|
| Herbicide: 2-chloro-2',6'-diethyl-N—(2''-propoxyethyl)-acetanilide, "Pretilachlor" | | | |
| 1 | 2 | 2 | 62.5 |
| 2 | 2 | 2 | 50 |
| 49 | 2 | 2 | 50 |
| 50 | 2 | 2 | 50 |
| 53 | 2 | 2 | 62.5 |
| 54 | 2 | 2 | 50 |
| 59 | 2 | 2 | 50 |
| 84 | 2 | 2 | 62.5 |
| 99 | 2 | 2 | 37.5 |
| Herbicide: 2-chloro-2',6'-diethyl-N—(butoxymethyl)-acetanilide, "Butolachlor" | | | |
| 1 | 3 | 3 | 25 |
| 2 | 3 | 3 | 25 |
| 49 | 3 | 3 | 37.5 |
| 50 | 3 | 3 | 37.5 |
| 53 | 3 | 3 | 25 |
| 54 | 3 | 3 | 37.5 |
| Herbicide: 2-chloro-2',6'-diethyl-N—(methoxymethyl)-acetanilide, "Alachlor" | | | |
| 1 | 0.25 | 0.25 | 37.5 |
| 2 | 0.5 | 0.5 | 25 |
| 49 | 0.5 | 0.5 | 12.5 |

EXAMPLE 25

Test with antidote and herbicide in dry rice. Application of the antidote as seed dressing Rice seeds of the IR-36 variety are mixed with the test antidote in a glass container. Seeds and test compound are well mixed by shaking and rotating. Containers measuring 47 cm×29 cm×24 cm are then filled with sandy loam and the dressed seeds are sown therein. The seeds are covered and the herbicide is then sprayed onto the surface of the soil. The protective action of the antidote is evaluated in percent 18 days after sowing. The plants treated with herbicide alone (no protective action) as well as the completely untreated controls (100% growth) serve as references for the evaluation. The results are as follows:

| Antidote compound | Rate of application in g per kg of seeds | Herbicide rate of application in kg/ha | Protective action in % |
|---|---|---|---|
| Herbicide: 2-chloro-6'-ethyl-N—(2''-methoxy-1''-methylethyl)-acet-o-toluidide, "Metolachlor" | | | |
| 1 | 1 g | 0.5 | 62.5 |
| Herbicide: 2-chloro-2,6-diethyl-N—(2''-propoxyethyl)-acetanilide, "Pretilachlor" | | | |
| 1 | 2 g | 3 | 37.5 |

EXAMPLE 26

Tests with antidote and herbicide in soybeans. Preemergence application of antidote and herbicide as tank mixture Flower pots having a diameter of 6 cm at the top are filled with sandy loam and soybean seeds of the "Hark" variety are sown therein. The seeds are covered and a dilute solution of the test antidote together with the herbicide is then sprayed as tank mixture onto the surface of the soil. Evaluation of the protective action in percent is made 21 days after the application of the herbicide. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: 4-amino-6-tert-butyl-4,5-dihydro-3-methylthio-1,2,4-triazin-S—one, "Metribuzin" | | | |
| 1 | 0.5 | 0.5 | 25 |

EXAMPLE 27

Test with antidote and herbicide in sorghum. Preemergence application of antidote and herbicide as tank mixture Flower pots having a diameter of 6 cm at the top are filled with sandy loam and sorghum seeds of the "Funk G 522" variety are sown therein. The seeds are covered and a dilute solution of the test antidote together with the herbicide is then sprayed as tank mixture onto the surface of the soil. Evaluation of the protective action in percent is made 14 days after the application of the herbicide. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: 2-chloro-6'-ethyl-N—(2''-methoxy-1''-methylethyl)-acet-o-toluidide, "Metolachlor" | | | |
| 468 | 1.5 | 1.5 | 37.5 |

EXAMPLE 28

Test with antidote and herbicide in wheat. Preemergence application of antidote and herbicide as tank mixture Wheat seeds are sown in a greenhouse in plastic pots which contain 0.5 l of garden soil. The plants are then treated postemergence in the 2–3-leaf stage with the test antidote together with the herbicide as tank mixture. Evaluation of the protective action of the antidote in percent is made 20 days after application. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: α-[4-(3',5'-dichloropyridyloxy-2'-)phenoxy]-propionic acid propinyl ester | | | |
| 54 | 0.5 | 0.5 | 50 |
| 132 | 0.5 | 0.5 | 25 |
| 197 | 0.5 | 0.5 | 25 |
| 461 | 0.5 | 0.5 | 37.5 |

EXAMPLE 29

Test with antidote and herbicide in cereals.
Preemergence application of antidote and herbicide as tank mixture Wheat or barley are sown in a greenhouse in plastic pots having a diameter at the top of 11 cm and containing 0.5 l of garden soil. The seeds are covered and a dilute solution of the test antidote together with the herbicide is then sprayed as tank mixture onto the surface of the soil. Evaluation of the protective action in percent is made 24 days after the application of the herbicide. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: 2-chloro-6'-ethyl-N—(2''-methoxy-1''-methylethyl)-acet-o-toluidide, "Metolachlor" | | | |
| Wheat (Farnese variety) | | | |
| 2 | 1 | 1 | 25 |
| Barley | | | |
| 1 | 1 | 1 | 25 |

EXAMPLE 30

Test with antidote and herbicide in maize.
Preemergence application of antidote and herbicide as tank mixture Maize seeds of the "LG 5" variety are sown in a greenhouse in plastic pots having a diameter at the top of 11 cm and containing 0.5 l of garden soil. The seeds are covered and a dilute solution of the test antidote together with the herbicide is then sprayed as tank mixture onto the surface of the soil. Evaluation of the protective action in percent is made 18 days after the application of the herbicide. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: 2-chloro-2',6'-dimethyl-N—(2''-methoxy-1''-methylethyl)-acetanilide | | | |
| 2 | 2 | 2 | 25 |

EXAMPLE 31

Test with antidote and herbicide in maize. Application of the antidote as seed dressing Maize seeds of the "LG 5" variety are mixed with the test antidote in a glass container. Seeds and compound are well mixed by shaking and rotation. Plastic pots having a diameter of 11 cm at the top are then filled with garden soil and the dressed seeds are sown therein. The seeds are covered and the herbicide is then applied preemergence. Evaluation of the protective action of the antidote in percent is then made 18 days after the application of the herbicide. The plants treated with herbicide alone (no protective action) as well as the completely untreated controls (100% growth) serve as references for the evaluation. The result is as follows:

| Antidote compound | Rate of application in kg/ha | Herbicide rate of application in kg/ha | Protective action in % |
|---|---|---|---|
| Herbicide: 2-chloro-2',6'-dimethyl-N—(methoxyethyl)-acetanilide, "Dimetolachlor" | | | |
| 2 | 2 | 0.5 | 25 |

What is claimed is:

1. Seeds of cereal plants selected from the group consisting of rice, sorghum, wheat, barley, maize, rye and oats, coated with a compound of the formula

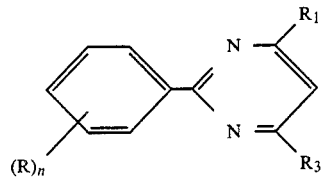

in which
each of $R_1$ and $R_3$ is chlorine, bromine or fluorine,
each of R is hydrogen, methyl, chlorine, bromine, fluorine, methoxy, nitro, hydroxy, trifluoromethyl, ethynyl, amino, acetamido, carboxy, carbomethoxy or acetamidosulfonyl, and
n is 1 or 2,
wherein the compound is coated on to the seed in an antidotally effective amount ranging from 0.1 to 10 grams per kilogram of seed.

2. Seeds according to claim 1 in which, in the compound, n is 1 and R is in the para-position.

3. Seeds according to claim 2 in which the compound is 2-phenyl-4,6-dichloropyrimidine.

4. Seeds according to claim 2 in which the compound is 2-phenyl-4,6-dibromopyrimidine.

5. Seeds according to claim 2 in which the compound is 2-(para-tolyl)-4,6-dichloropyrimidine.

6. Seeds according to claim 2 in which the compound is 2-(4-chlorophenyl)-4,6-dichloropyrimidine.

7. Seeds according to claim 2 in which the compound is 2-(4-methoxyphenyl)-4,6-dichloropyrimidine.

8. Seeds according to claim 2 in which the compound is 2-(4-hydroxyphenyl)-4,6-dichloropyrimidine.

9. Seeds according to claim 2 in which the compound is 2-(3-nitrophenyl)-4,6-dichloropyrimidine.

10. Seeds according to claim 1 in which the compound is 2-(3-chloro-4-fluorophenyl)-4,6-dichloropyrimidine.

11. Seeds according to claim 1 which are coated with from 1 to 2 grams of the compound per kilogram of seed.

12. Seeds according to claim 1 which are rice or maize seeds.

13. Seeds according to claim 1, the plants grown from which are resistant to injury by application of a chloroacetanilide herbicide.

14. Rice seeds according to claim 13 in which the herbicide is pretilachlor.

15. Rice seeds according to claim 13 in which the herbicide is metolachlor.

16. Maize seeds according to claim 13 in which the herbicide is metolachlor.

* * * * *

UNITED STATES PATENT AND TRADEMARK OFFICE
CERTIFICATE OF CORRECTION

PATENT NO. : 4,674,229

DATED : June 23, 1987

INVENTOR(S) : Kurt Burdeska, Anni Kabas-Maskulinski, legal heir of Guglielmo Kabas, deceased, Hans-Georg Brunner, Werner Föry It is certified that error appears in the above-identified patent and that said Letters Patent is hereby corrected as shown below:

On the cover page, Item 30, line 1, should read --
Dec. 23, 1980 [CH] Switzerland .............9522/80--.

Signed and Sealed this

Fifth Day of January, 1988

Attest:

DONALD J. QUIGG

Attesting Officer      Commissioner of Patents and Trademarks